(12) United States Patent
Nakamura et al.

(10) Patent No.: US 9,639,932 B2
(45) Date of Patent: May 2, 2017

(54) IMAGE PROCESSING DEVICE, IMAGE PROCESSING METHOD, PROGRAM, AND RECORDING MEDIUM FOR DETECTION OF EPIDERMIS PATTERN

(71) Applicant: Sony Corporation, Tokyo (JP)

(72) Inventors: Yusuke Nakamura, Chiba (JP); Shinichiro Gomi, Tokyo (JP)

(73) Assignee: Sony Corporation (JP)

( * ) Notice: Subject to any disclaimer, the term of this patent is extended or adjusted under 35 U.S.C. 154(b) by 0 days.

(21) Appl. No.: 14/718,647

(22) Filed: May 21, 2015

(65) Prior Publication Data

US 2015/0254847 A1    Sep. 10, 2015

Related U.S. Application Data

(62) Division of application No. 13/462,949, filed on May 3, 2012, now Pat. No. 9,122,906.

(30) Foreign Application Priority Data

May 23, 2011    (JP) .................................. 2011-115182

(51) Int. Cl.
G06K 9/00    (2006.01)
G06T 7/00    (2017.01)
G06T 7/40    (2017.01)
G06K 9/46    (2006.01)
G06K 9/52    (2006.01)

(52) U.S. Cl.
CPC .......... *G06T 7/0012* (2013.01); *G06K 9/0014* (2013.01); *G06K 9/46* (2013.01); *G06K 9/52* (2013.01); *G06T 7/40* (2013.01); *G06K 2009/4666* (2013.01); *G06T 2207/30088* (2013.01)

(58) Field of Classification Search
None
See application file for complete search history.

(56) References Cited

U.S. PATENT DOCUMENTS

2002/0126883 A1    9/2002  Senior
2008/0304736 A1*  12/2008  Nakagawa ........... A61B 5/0059
                                                      382/165
2009/0054744 A1    2/2009  Kitamura et al.

FOREIGN PATENT DOCUMENTS

JP    2006-061170 A    3/2006
JP    2006-305184 A    11/2006

* cited by examiner

*Primary Examiner* — Atiba O Fitzpatrick
(74) *Attorney, Agent, or Firm* — Lerner, David, Littenberg, Krumholz & Mentlik, LLP

(57) ABSTRACT

An epidermis pattern detection unit detects epidermis patterns in an epidermis image captured from the epidermis of skin by an epidermis image capturing unit. An acquired element analysis unit analyzes uniformity of shapes of the epidermis patterns in the epidermis image. A texture evaluation unit evaluates a texture state of the skin based on the uniformity of shapes of the epidermis patterns. The present technology, for example, may be applied to systems that evaluate the texture state of the skin.

6 Claims, 28 Drawing Sheets

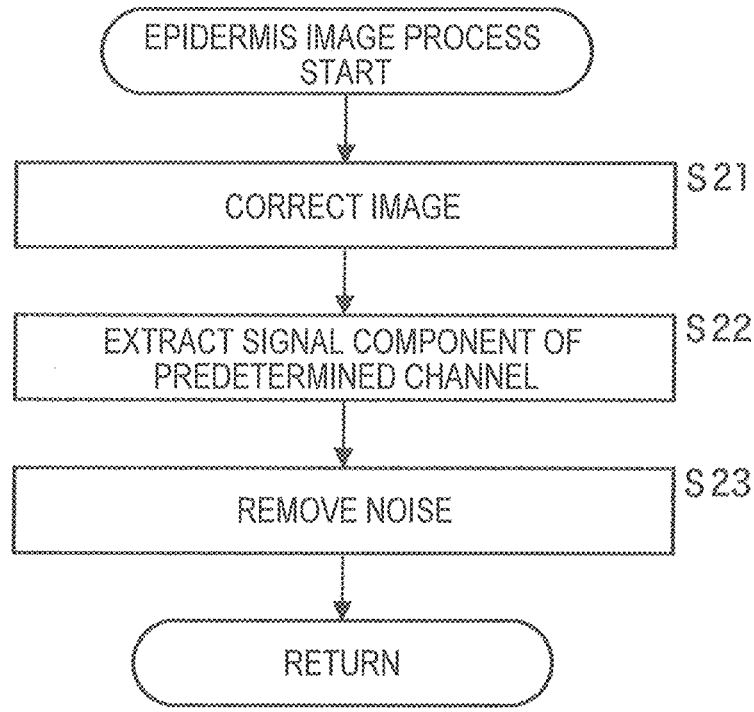
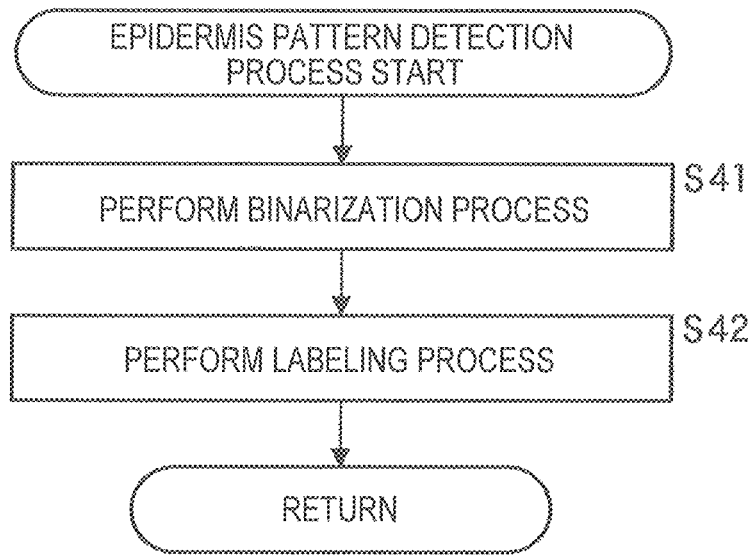

FIG. 15
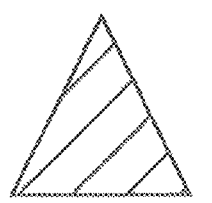 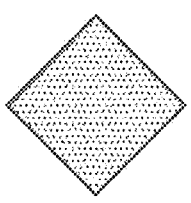 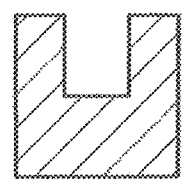 
Shape0   Shape1   Shape2   Shape3

FIG. 22

| eval3 total | COMPREHENSIVE DETERMINATION VALUE (EVALUATION) |
|---|---|
| 0.8~1.0 | A (Excellent) |
| 0.6~0.8 | B (Very Good) |
| 0.4~0.6 | C (Good) |
| 0.2~0.4 | D (Fair) |
| 0.0~0.2 | E (Poor) |

IMAGE PROCESSING DEVICE, IMAGE PROCESSING METHOD, PROGRAM, AND RECORDING MEDIUM FOR DETECTION OF EPIDERMIS PATTERN

CROSS-REFERENCE TO RELATED APPLICATIONS

The present application is a divisional of U.S. application Ser. No. 13/462,949, filed May 3, 2012 which claims benefit of Japanese Patent Application No. JP-2011-115182, filed May 23, 2011, the disclosures of which are incorporated herein by reference.

BACKGROUND

The present technology relates to an image processing device, an image processing method, a program, and a recording medium, and more particularly, to an image processing device, an image processing method, a program, and a recording medium, which are suitable for evaluating texture states of skin.

Techniques for evaluating texture states of skin by analyzing a skin image captured from the skin of a human are proposed in related art.

For example, a technique of evaluating the fineness of the texture by means of the number of skin ridges in the skin image, and evaluating the orientation of the texture based on spectral shapes of the image Fourier-transformed from the skin image is proposed (see Japanese Patent Laid-Open Publication No. 2006-61170).

For example, another technique of analyzing the textures or pores of the skin based on sizes of the pores in the skin image, clearness of the skin grooves, fineness of the skin ridges, and a degree of circularity of the skin ridges is proposed (see Japanese Patent Laid-Open Publication No. 2006-305184).

SUMMARY

However, in the technique disclosed in Japanese Patent Laid-Open Publication No. 2006-61170, the texture state of the skin may not be evaluated correctly because shapes of the textures are not taken into consideration. In addition, since the shapes of the skin ridges vary vastly, the texture state of the skin may not be evaluated correctly even when the degree of circularity of the skin ridges is taken into consideration in accordance with the technique disclosed in Japanese Patent Laid-Open Publication No. 2006-305184.

The present technology is made to enable the texture state of the skin to be evaluated.

According to a first aspect of the present technology, there is provided an image processing device, which includes an epidermis pattern detection unit configured to detect epidermis patterns that are patterns of an epidermis in an epidermis image captured from the epidermis of skin, an analysis unit configured to analyze uniformity of shapes of the epidermis patterns, and an evaluation unit configured to evaluate a texture state of the skin based on the uniformity of shapes of the epidermis patterns.

The analysis unit may further analyze at least one of uniformity of sizes of the epidermis patterns and uniformity of distributions of edge directions of the epidermis patterns, and the evaluation unit may further evaluate the texture state of the skin based on at least one of the uniformity of sizes of the epidermis patterns and the uniformity of distribution of edge directions of the epidermis patterns.

The analysis unit may further analyze a ratio at which the epidermis patterns have predetermined shapes, and the evaluation unit may further evaluate the texture state of the skin based on the ratio at which the epidermis patterns have the predetermined shapes.

The epidermis patterns may be patterns formed on the epidermis by skin ridges or skin grooves.

According to the first aspect of the present technology, there is provided an image processing method performed by an image processing device configured to evaluate a texture state of skin, which includes detecting epidermis patterns that are patterns of an epidermis in an epidermis image captured from the epidermis of the skin, analyzing uniformity of shapes of the epidermis patterns, and evaluating the texture state of the skin based on the uniformity of shapes of the epidermis patterns.

According to the first aspect of the present technology, there is provided a program for causing a computer to execute operations including detecting epidermis patterns that are patterns of an epidermis in an epidermis image captured from the epidermis of skin, analyzing uniformity of shapes of the epidermis patterns, and evaluating a texture state of the skin based on the uniformity of shapes of the epidermis patterns.

According to a second aspect of the present technology, there is provided an image processing device, which includes an epidermis pattern detection unit configured to detect epidermis patterns that are patterns of an epidermis in an epidermis image captured from the epidermis of skin, an acquired element analysis unit configured to analyze acquired elements among elements indicating a texture state of the skin based on the detected epidermis patterns, an inherent element analysis unit configured to analyze inherent elements among the elements indicating the texture state of the skin based on the detected epidermis patterns, and an evaluation unit configured to evaluate the texture state of the skin based on the analysis result from the acquired elements and the analysis result from the inherent elements.

The acquired element analysis unit may analyze, as the acquired elements, at least one of uniformity of shapes of the epidermis patterns, uniformity of sizes of the epidermis patterns, and uniformity of distribution of edge directions of the epidermis patterns, and the inherent element analysis unit may analyze, as the inherent elements, the number of the epidermis patterns per unit area.

The evaluation unit may calculate an evaluation value of the texture state of the skin by weighting and adding an evaluation value based on the analysis result from the acquired elements and an evaluation value based on the analysis result from the inherent elements.

The epidermis patterns may be patterns formed on the epidermis by skin ridges or skin grooves.

According to the second aspect of the present technology, there is provided an image processing method performed by an image processing device configured to evaluate a texture state of skin, which includes detecting epidermis patterns that are patterns of an epidermis in an epidermis image captured from the epidermis of the skin, analyzing acquired elements among elements indicating the texture state of the skin based on the detected epidermis patterns, analyzing inherent elements among the elements indicating the texture state of the skin based on the detected epidermis patterns, and evaluating the texture state of the skin based on the analysis result from the acquired elements and the analysis result from the inherent elements.

According to the second aspect of the present technology, there is provided a program for causing a computer to execute operations which includes detecting epidermis patterns that are patterns of an epidermis in an epidermis image captured from the epidermis of skin, analyzing acquired elements among elements indicating a texture state of the skin based on the detected epidermis patterns, analyzing inherent elements among the elements indicating the texture state of the skin based on the detected epidermis patterns, and evaluating the texture state of the skin based on the analysis result from the acquired elements and the analysis result from the inherent elements.

According to a third aspect of the present technology, there is provided an image processing device, which includes an epidermis pattern detection unit configured to detect epidermis patterns that are patterns of an epidermis in an epidermis image captured from the epidermis of skin, a dermis pattern detection unit configured to detect dermis patterns that are patterns of a dermis in a dermis image captured from the dermis of the skin, an acquired element analysis unit configured to analyze acquired elements among elements indicating a texture state of the skin based on the detected epidermis patterns, an inherent element analysis unit configured to analyze inherent elements among the elements indicating the texture state of the skin based on the detected dermis patterns, and an evaluation unit configured to evaluate the texture state of the skin based on the analysis result from the acquired elements and the analysis result from the inherent elements.

The acquired element analysis unit may analyze, as the acquired elements, at least one of uniformity of shapes of the epidermis patterns, uniformity of sizes of the epidermis patterns, and uniformity of distribution of edge directions of the epidermis patterns, and the inherent element analysis unit may analyze, as the inherent elements, at least one of uniformity of shapes of the dermis patterns, uniformity of sizes of the dermis patterns, uniformity of distribution of edge directions of the dermis patterns, and the number of the dermis patterns per unit area.

The inherent element analysis unit may further analyze, as the inherent element, the number of the epidermis patterns per unit area based on the detected epidermis patterns.

The evaluation unit may calculate an evaluation value of the texture state of the skin by weighting and adding an evaluation value based on the analysis result from the acquired elements and an evaluation value based on the analysis result from the inherent elements.

The epidermis patterns may be patterns formed on the epidermis by skin ridges or skin grooves, and the dermis patterns may be patterns formed on the dermis by papillary layers.

According to the third aspect of the present technology, there is provided an image processing method performed by an image processing device configured to evaluate a texture state of skin, which includes detecting epidermis patterns that are patterns of an epidermis in an epidermis image captured from the epidermis of the skin, detecting dermis patterns that are patterns of a dermis in a dermis image captured from the dermis of the skin, analyzing acquired elements among elements indicating the texture state of the skin based on the detected epidermis patterns, analyzing inherent elements among the elements indicating the texture state of the skin based on the detected dermis patterns, and evaluating the texture state of the skin based on the analysis result from the acquired elements and the analysis result from the inherent elements.

According to the third aspect of the present technology, there is provided a program for causing a computer to execute operations which includes detecting epidermis patterns that are patterns of an epidermis in an epidermis image captured from the epidermis of skin, detecting dermis patterns that are patterns of a dermis in a dermis image captured from the dermis of the skin, analyzing acquired elements among elements indicating a texture state of the skin based on the detected epidermis patterns, analyzing inherent elements among the elements indicating the texture state of the skin based on the detected dermis patterns, and evaluating the texture state of the skin based on the analysis result from the acquired elements and the analysis result from the inherent elements.

According to the first aspect of the present technology, epidermis patterns that are patterns of an epidermis in an epidermis image captured from the epidermis of the skin are detected, uniformity of shapes of the epidermis patterns is analyzed, and a texture state of the skin is evaluated based on the uniformity of the shapes of the epidermis patterns.

According to the second aspect of the present technology, epidermis patterns that are patterns of an epidermis in an epidermis image captured from the epidermis of skin are detected, acquired elements among elements indicating a texture state of the skin are analyzed based on the detected epidermis patterns, inherent elements among the elements indicating the texture state of the skin are analyzed based on the detected epidermis patterns, and the texture state of the skin is evaluated based on the analysis result from the acquired elements and the analysis result from the inherent elements.

According to the third aspect of the present technology, epidermis patterns that are patterns of an epidermis in an epidermis image captured from the epidermis of the skin are detected, dermis patterns that are patterns of a dermis in a dermis image captured from the dermis of the skin are detected, acquired elements among elements indicating the texture state of the skin are analyzed based on the detected epidermis patterns, inherent elements among the elements indicating the texture state of the skin are analyzed based on the detected dermis patterns, and the texture state of the skin is evaluated based on the analysis result from the acquired elements and the analysis result from the inherent elements.

According to the first to third aspects of the present technology described above, the texture state of the skin can be evaluated.

BRIEF DESCRIPTION OF THE DRAWINGS

FIG. 6 is a flow chart illustrating epidermis image processing;

FIG. 7 is a flow chart illustrating an epidermis pattern detection process;

FIG. 15 is a diagram illustrating examples of reference shapes;

FIG. 22 is a diagram illustrating an example of a table for obtaining comprehensive determination values;

DETAILED DESCRIPTION OF THE EMBODIMENT(S)

Figure 1:
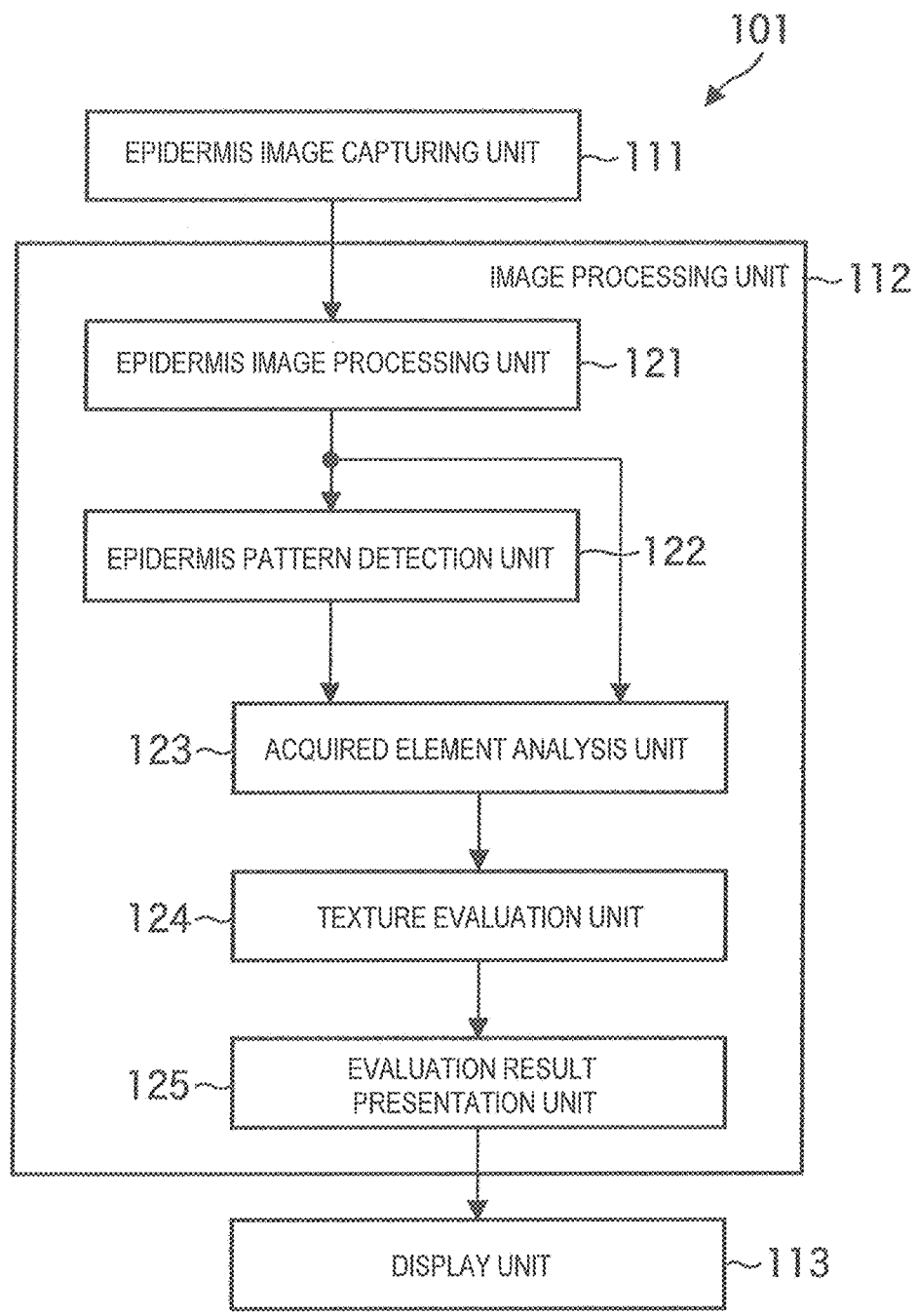
FIG. 1 is a block diagram illustrating an image processing system in accordance with a first embodiment of the present technology.

Hereinafter, preferred embodiments of the present technology will be described in detail with reference to the appended drawings. Note that, in this specification and the appended drawings, structural elements that have substantially the same function and structure are denoted with the same reference numerals, and repeated explanation of these structural elements is omitted.

Hereinafter, forms for embodying the present technology (which will be referred to as embodiments) will be described. The description is made in the following order.
1. First embodiment (example of analyzing acquired elements only)
2. Second embodiment (example of analyzing both acquired elements and inherent elements)
3. Third embodiment (example of analyzing both epidermis and dermis)
4. Modification 1. First Embodiment First, a first embodiment of the present technology will be described with reference to FIGS. 1 to 15.

[Configuration Example of Image Processing System 101]

FIG. 1 is a block diagram illustrating a configuration example of an image processing system 101 in accordance with the first embodiment of the present technology.

The image processing system 101 captures the epidermis of skin of a human to be evaluated (hereinafter referred to as an evaluation target), and evaluates the texture state of the skin of the evaluation target based on the captured image (hereinafter referred to as an epidermis image).

The image processing system 101 includes an epidermis image capturing unit 111, an image processing unit 112, and a display unit 113.

The epidermis image capturing unit 111 captures the epidermis of the skin of the evaluation target, and supplies the captured epidermis image to an epidermis image processing unit 121 of the image processing unit 112.

In addition, the epidermis image capturing unit 111 is not limited to specific kinds of capturing devices but may be employed for any kind of capturing device.

However, it is preferable that the epidermis image capturing unit 111 have a manual focus adjusting function, a light source (e.g., light emitting diode (LED)) capable of uniformly irradiating illumination light over an entire object, and a micro-lens capable of performing capturing enough to recognize the surface structure of the skin. Further, it is preferable that the epidermis image capturing unit 111 have an attachment to be in closer contact with the skin than the lens in order to perform every single capturing with the fixed focus position. In this case, the attachment may have a light blocking function for preventing effects of external light.

In addition, it is preferable that the wavelength range of the light source of the epidermis image capturing unit 111 be a visible range (400 to 700 nm). In a similar way, the spectral sensitivity of the image sensor of the epidermis image capturing unit 111 may also be one corresponding to the typical RGB where the sensitivity lies within the visible range. However, it is preferable that the sensitivity of the short wavelength side be higher.

The image processing unit 112 performs segmentation (regional division) on the epidermis image, and evaluates the texture of the skin of the evaluation target based on the segmentation result.

The image processing unit 112 includes an epidermis image processing unit 121, an epidermis pattern detection unit 122, an acquired element analysis unit 123, a texture evaluation unit 124, and an evaluation result presentation unit 125.

The epidermis image processing unit 121, as will be described below, performs predetermined image processing such as correction or noise removal on the epidermis image, and supplies the image-processed epidermis image to the epidermis pattern detection unit 122 and the acquired element analysis unit 123.

The epidermis pattern detection unit 122, as will be described below, detects patterns of the epidermis within the epidermis image that are formed on the epidermis by skin ridges or skin grooves (hereinafter referred to as epidermis patterns), and supplies the detection result (hereinafter referred to as epidermis pattern detection result) to the acquired element analysis unit 123.

The acquired element analysis unit 123, as will be described below, analyzes acquired elements among elements indicating the texture state of the skin based on the image-processed epidermis image and the epidermis pattern detection result. The acquired element analysis unit 123 supplies the analysis result to the texture evaluation unit 124.

The texture evaluation unit 124 evaluates the texture state of the skin of the evaluation target based on the analysis result from the acquired element analysis unit 123, and supplies the evaluation result to the evaluation result presentation unit 125.

The evaluation result presentation unit 125 causes the display unit 113 to display information indicating the evaluation result of the texture state of the skin of the evaluation target.

The display unit 113 is not limited to specific kinds of display devices but may be employed for any kind of display device. In addition, the display unit 113 may be disposed to be exclusive for the image processing system 101, or display devices of other apparatuses such as television receivers or mobile phones may be employed for the display unit.

[Configuration Example of Epidermis Image Processing Unit 121 and Epidermis Pattern Detection Unit 122]

Figure 2:
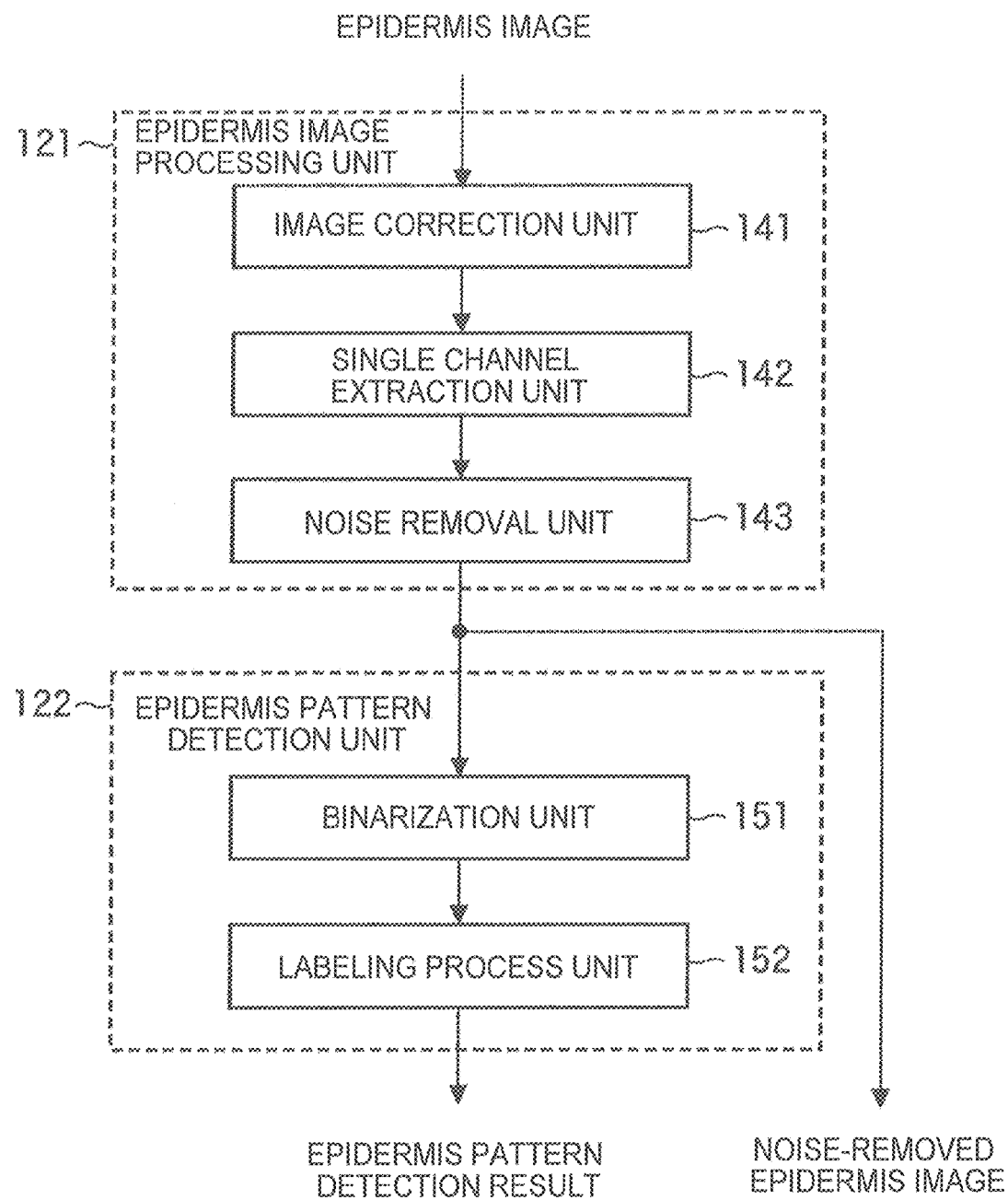
FIG. 2 is a block diagram illustrating a configuration example of an epidermis image processing unit and an epidermis pattern detection unit.

FIG. 2 is a block diagram illustrating a configuration example of functions of the epidermis image processing unit 121 and the epidermis pattern detection unit 122.

The epidermis image processing unit 121 includes an image correction unit 141, a single channel extraction unit 142, and a noise removal unit 143. In addition, the epidermis pattern detection unit 122 includes a binarization unit 151 and a labeling process unit 152.

The image correction unit 141 performs predetermined image correction such as distortion correction or reduction of the epidermis image, and supplies the corrected epidermis image to the single channel extraction unit 142.

The single channel extraction unit 142 extracts signal components of a predetermined channel from the corrected epidermis image, and supplies the epidermis image composed of the extracted signal components (hereinafter referred to as a single channel epidermis image) to the noise removal unit 143.

The noise removal unit 143 removes noise of the single channel epidermis image, and supplies the single channel epidermis image from which the noise is removed (hereinafter referred to as a noise-removed epidermis image) to the binarization unit 151 of the epidermis pattern detection unit 122 and the acquired element analysis unit 123.

The binarization unit 151 performs binarization on the noise-removed epidermis image, and supplies the binarized image (hereinafter referred to as a binarized epidermis image) to the labeling process unit 152.

The labeling process unit 152 performs a labeling process on the binarized epidermis image to detect the epidermis patterns. In particular, the labeling process unit 152 detects regions of the skin ridges within the epidermis image (hereinafter referred to as skin ridge regions) as the epidermis patterns. In addition, the labeling process unit 152 counts the number of skin ridge regions within the epidermis image. And the labeling process unit 152 supplies the epidermis pattern detection result indicating the detection result of the number of skin ridges and the skin ridge regions to the acquired element analysis unit 123.

[Configuration Example of Acquired Element Analysis Unit 123]

Figure 3:
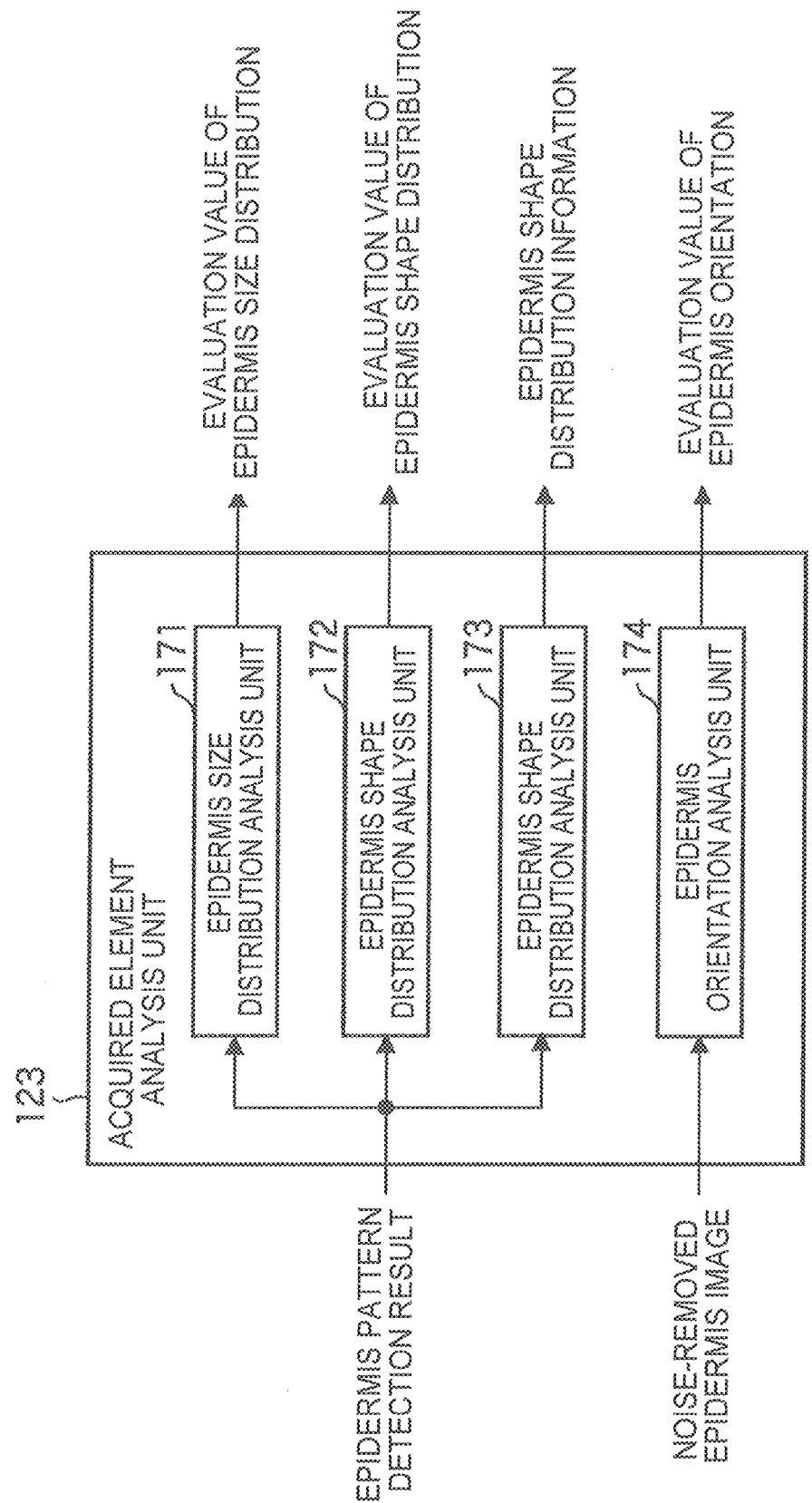
FIG. 3 is a block diagram illustrating a configuration example of an acquired element analysis unit.

FIG. 3 is a block diagram illustrating a configuration example of the function of the acquired element analysis unit 123. The acquired element analysis unit 123 includes an epidermis size distribution analysis unit 171, an epidermis shape distribution analysis unit 172, an epidermis shape distribution analysis unit 173, and an epidermis orientation analysis unit 174.

The epidermis size distribution analysis unit 171 analyzes the distribution of sizes of the epidermis patterns. In particular, the epidermis size distribution analysis unit 171 analyzes the distribution of sizes of the skin ridge regions, and calculates the evaluation value of the epidermis size distribution indicating the uniformity of sizes of the skin ridge regions. The epidermis size distribution analysis unit 171 supplies the calculated evaluation value of the epidermis size distribution to the texture evaluation unit 124.

The epidermis shape distribution analysis unit 172 analyzes the distribution of shapes of the epidermis patterns. In particular, the epidermis shape distribution analysis unit 172 analyzes the distribution of shapes of the skin ridge regions, and calculates the evaluation value of the epidermis shape distribution indicating the uniformity of shapes of the skin ridge regions. The epidermis shape distribution analysis unit 172 supplies the calculated evaluation value of the epidermis shape distribution to the texture evaluation unit 124.

The epidermis shape distribution analysis unit 173 analyzes the distribution of shapes of the epidermis patterns from a point of view different from the epidermis shape distribution analysis unit 172. In particular, the epidermis shape distribution analysis unit 173 compares each of the skin ridge regions with predetermined reference shapes, and obtains epidermis shape distribution information indicating ratios of the skin ridge regions having shapes close to each of the reference shapes. The epidermis shape distribution analysis unit 173 supplies the obtained epidermis shape distribution information to the texture evaluation unit 124.

The epidermis orientation analysis unit 174 analyzes the orientation of the epidermis patterns. In particular, the epidermis orientation analysis unit 174 analyzes the distribution of edge directions of the skin ridge regions, and calculates the evaluation value of the epidermis orientation indicating the uniformity of the distribution of edge directions of the skin ridge regions. The epidermis orientation analysis unit 174 supplies the calculated evaluation value of the epidermis orientation to the texture evaluation unit 124.

In addition, the sizes, the shapes, and the edge directions of the skin ridges vary in an acquired manner depending on aging, health, skin care and so forth. Accordingly, the evaluation value of the epidermis size distribution, the evaluation value of the epidermis shape distribution, the epidermis shape distribution information, and the evaluation value of the epidermis orientation become indexes for evaluating the acquired property of the texture state of the skin.

[Configuration Example of Epidermis Orientation Analysis Unit 174]

Figure 4:
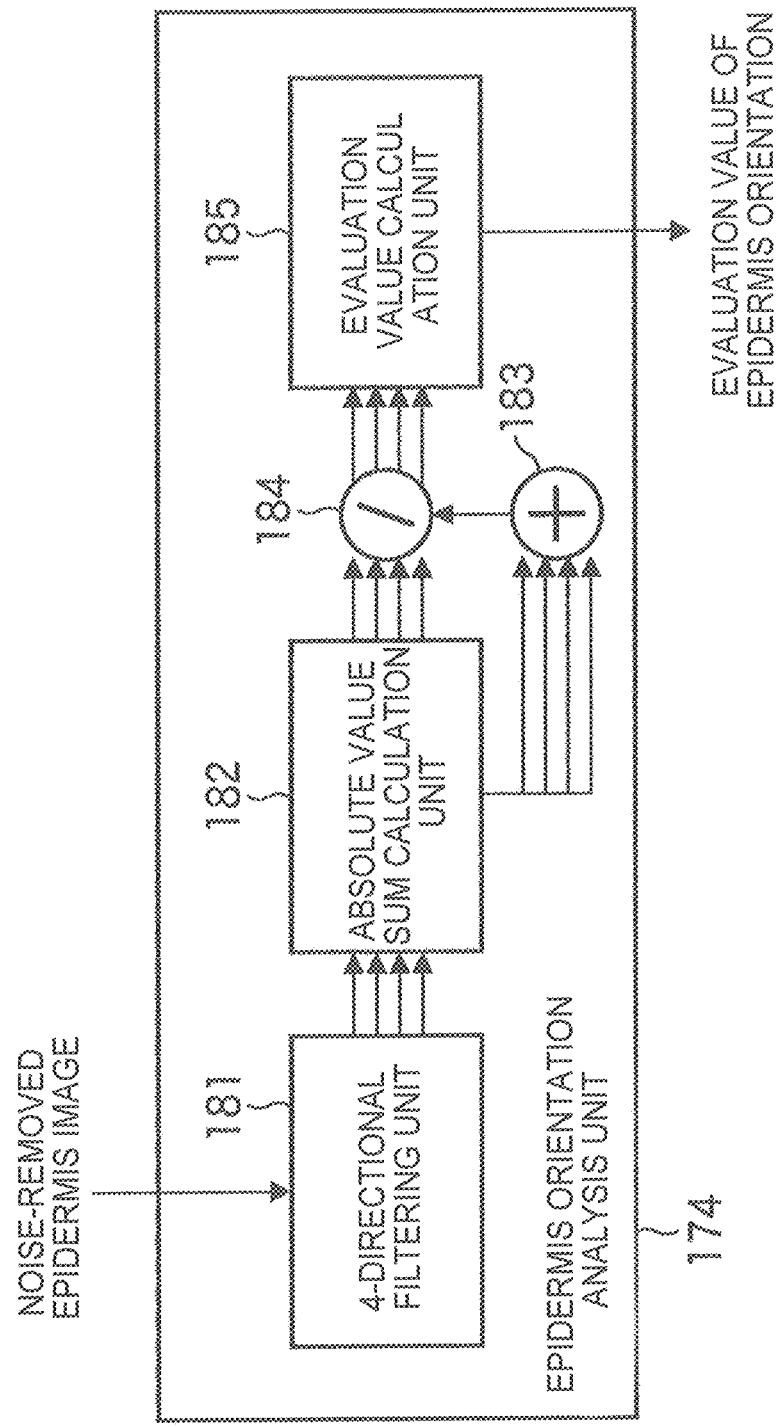
FIG. 4 is a block diagram illustrating a configuration example of an epidermis orientation analysis unit.

FIG. 4 is a block diagram illustrating the configuration example of the epidermis orientation analysis unit 174.

The epidermis orientation analysis unit 174 includes a four-directional filtering unit 181, an absolute value sum calculation unit 182, an addition unit 183, a division unit 184, and an evaluation value calculation unit 185.

The four-directional filtering unit 181 performs edge filtering on the noise-removed epidermis image with respect to four directions such as 0°, 45°, 90°, and 135°. And the four-directional filtering unit 181 supplies the obtained four filter output images to the absolute value sum calculation unit 182.

The absolute value sum calculation unit 182 calculates the sum of absolute values of pixels within the image in each of the four filter output images. The absolute value sum calculation unit 182 then supplies the sum of the absolute values of the pixels within each of the four filter output images to the addition unit 183 and the division unit 184.

The addition unit 183 integrates the sum of the absolute values of the pixels of the respective filter output images, and supplies the obtained integrated value to the division unit 184.

The division unit 184 divides the sum of the absolute values of the pixels of each of the filter output images by the integrated value supplied from the addition unit 183, and supplies the obtained value to the evaluation value calculation 185.

The evaluation value calculation 185 calculates the evaluation value of the epidermis orientation based on the calculation values calculated by the division unit 184, and supplies the calculated evaluation value of the epidermis orientation to the texture evaluation unit 124.

[Texture Evaluation Process]

Next, a texture evaluation process executed by the image processing system 101 will be described with reference to the flow chart shown in FIG. 5.

In addition, this texture evaluation process is initiated, for example, when an instruction to execute the texture evaluation process is input through an input unit not shown in the image processing system 101.

In step S1, the epidermis image capturing unit 111 captures the epidermis image. That is, the epidermis image capturing unit 111 captures the epidermis of the skin of the portion to be evaluated in the evaluation target (e.g., cheeks, forehead, and so forth), and supplies the captured epidermis image to the image correction unit 141.

In step S2, the epidermis image processing unit 121 processes the epidermis image.

[Epidermis Image Processing]

Here, the epidermis image processing will be described in detail with reference to the flow chart shown in FIG. 6.

In step S21, the image correction unit 141 corrects the image. For example, shading distortion or lens distortion occurring on outer edges of the epidermis image may be considered. Accordingly, the image correction unit 141, for example, performs shading correction or lens distortion correction on the epidermis image, or cuts out a central region of the epidermis image.

In addition, the image correction unit 141, for example, reduces the corrected image in order to lower the processing cost.

In addition, hereinafter, unless otherwise noted, the size of the corrected epidermis image corresponds to 160 vertical× 120 horizontal pixels.

The image correction unit 141 supplies the corrected epidermis image to the single channel extraction unit 142.

In step S22, the single channel extraction unit 142 extracts signal components of a predetermined channel from the corrected epidermis image. For example, the single channel extraction unit 142 extracts the signal components of the blue (B) channel from the corrected epidermis image. The single channel extraction unit 142 then supplies the single channel epidermis image composed of the extracted signal components to the noise removal unit 143.

In addition, when a spectral camera is used as the epidermis image capturing unit 111, this processing may be omitted.

In step S23, the noise removal unit 143 removes the noise of the single channel epidermis image. For example, the noise removal unit 143 applies a smoothing filter to the single channel epidermis image.

In particular, the noise removal unit 143, for example, applies an edge preservation type smoothing filter to the single channel epidermis image in order to remove random noise or texture components on the skin ridges or skin grooves. For example, a bilateral filter of which the kernel size corresponds to 3×3 pixels, $\sigma_{space}$=15, and $\sigma_{color}$=15 is used as the edge preservation type smoothing filter.

Next, the noise removal unit 143, for example, applies an isolated point removal filter to the single channel epidermis image in order to remove specular reflection components or high brightness regions due to effects such as sweat glands. For example, a median filter of 3×3 pixels is used as the isolated point removal filter.

In addition, since such a noise removal process significantly depends on the capturing environment or performance of the epidermis image capturing unit 111, it is preferable that filters, parameters, and so forth to be applied be properly changed.

The noise removal unit 143 supplies the noise-removed epidermis image that is the single channel epidermis image with noise removed to the binarization unit 151 of the epidermis pattern detection unit 122 and the epidermis orientation analysis unit 174 of the acquired element analysis unit 123.

Accordingly, the epidermis image processing is finished.

Referring back to FIG. 5, in step S3, the epidermis pattern detection unit 122 performs the epidermis pattern detection process.

[Epidermis Pattern Detection Process]

Here, details of the epidermis pattern detection process will be described with reference to the flow chart shown in FIG. 7.

In step S41, the binarization unit 151 performs a binarization process. In particular, the binarization unit 151 binarizes the noise-removed epidermis image in order to perform segmentation on the skin ridges and skin grooves on the assumption that bright regions are protruding skin ridges and dark regions are recessed skin grooves in the epidermis image under the uniform light source.

For example, the binarization unit 151 performs the adaptive local binarization on the noise-removed epidermis image in order to further reduce effects of external light such as shading. For example, the binarization unit 151 calculates the total sum using Gaussians as weights with respect to nearby regions and uses, as a threshold value, a value obtained by subtracting a predetermined value bin_param from the total sum based on Equations (1a) and (1b) below, thereby binarizing the noise-removed epidermis image.

$$I(x, y) \leq \sum_{x,y \in \Omega} [G(x, y) \cdot I(x, y)] - \text{bin\_param} : I_{bin}(x, y) = Ib \quad (1a)$$

$$I(x, y) > \sum_{x,y \in \Omega} [G(x, y) \cdot I(x, y)] - \text{bin\_param} : I_{bin}(x, y) = Iw \quad (1b)$$

I(x, y) indicates the pixel value of the pixel of the coordinate(x, y) in the noise-removed epidermis image, G(x, y) indicates the Gaussian function, and $I_{bin}$(x, y) indicates the pixel value of the pixel of the coordinate (x, y) in the binarized epidermis image. In addition, Ib indicates the pixel value of black, and Iw indicates the pixel value of white.

In addition, the value of bin_param is suitably set so as to properly separate the skin ridge regions and the skin groove regions within the epidermis image.

The binarization unit 151 performs binarization on all pixels of the noise-removed epidermis image while shifting the block of interest by one pixel, thereby generating the binarized epidermis image. The binarization unit 151 then supplies the generated binarized epidermis image to the labeling process unit 152.

In step S42, the labeling process unit 152 performs the 4-connected or 8-connected labeling from the outside on the binarized epidermis image. Here, the labeling process unit 152 detects a region surrounded with a white contour at the outermost side as one region, and ignores a black region or another region surrounded with a white contour even if it is present inside the region surrounded at the outermost side.

Figure 8:
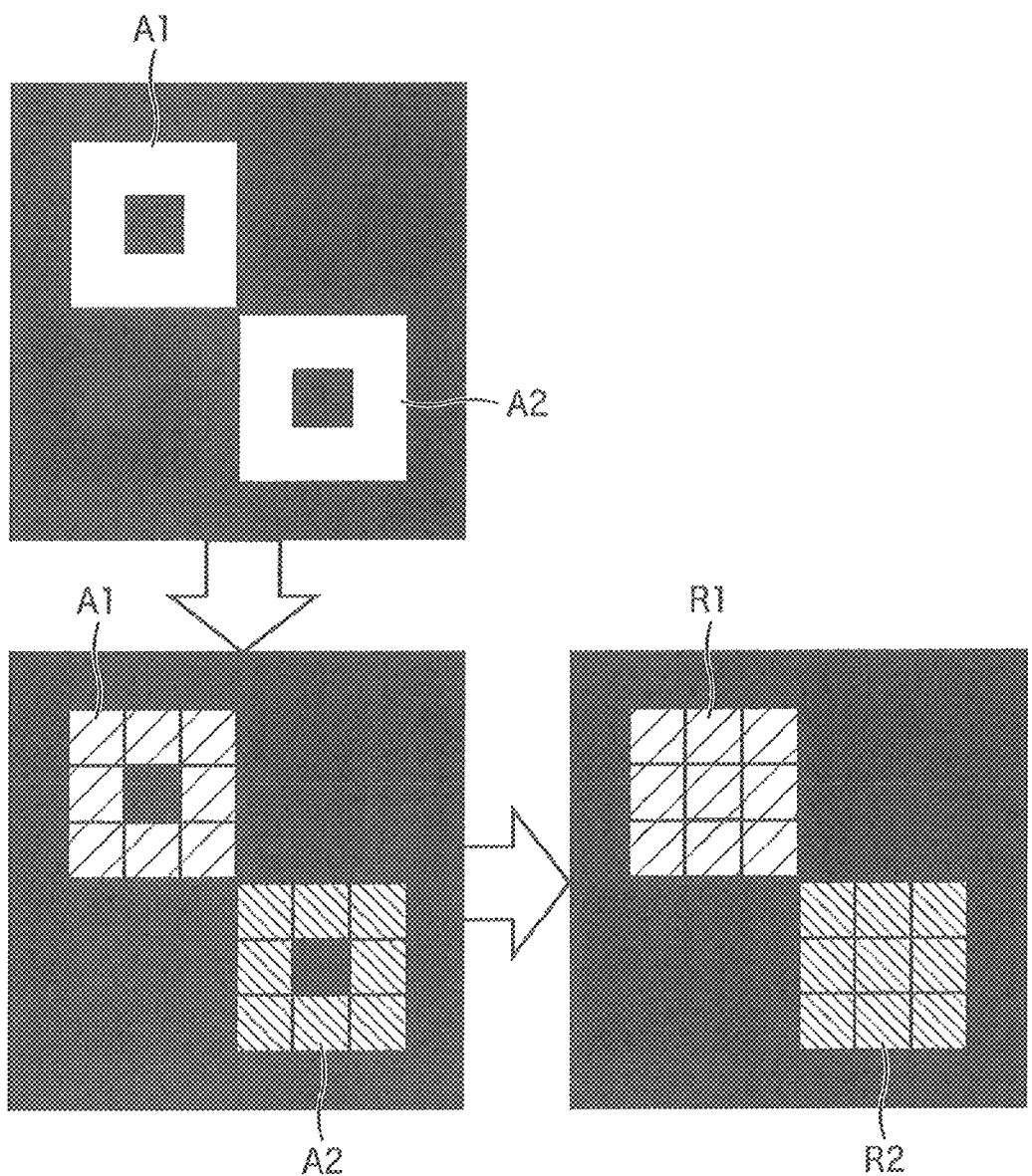
FIG. 8 is a diagram illustrating a specific example of a labeling process.

For example, as shown in FIG. 8, when the region A1 and the region A2 including black regions within regions surrounded with white contours are present in the binarized epidermis image, the region A1 and the region A2 are first recognized individually by the 4-connected labeling process. Further, since black regions within the region A1 and the region A2 are ignored, each of regions R1 and R2 having 3×3 pixels is recognized as one region, and is given with the labeling.

Accordingly, for example, dark regions due to recesses or the like within the skin ridges are ignored, so that it is possible to correctly detect the skin ridge regions.

In addition, hereinafter, regions given with the labeling by the labeling process are referred to as labeling regions.

In addition, in the skin of general people, an interval between the skin grooves is 0.25 to 0.5 mm. Considering that shapes of the skin ridges are usually triangles or quadrangles, the area of the skin ridge is thought to be about 0.031 to 0.25 mm$^2$.

Hence, the labeling process unit 152 obtains the proper range of the size of the skin ridge in the epidermis image based on the size of the image sensor of the epidermis image capturing unit 111 and so forth. The labeling process unit 152 then detects the region of a size within the obtained proper range among the detected labeling regions as the skin ridge region.

In addition, the labeling process unit 152 counts the number of detected skin ridge regions as the number of skin ridges $N_{ridge}$.

The labeling process unit 152 supplies the epidermis pattern detection result indicating the detecting result of the number of skin ridges $N_{ridge}$ and the skin ridge regions to the epidermis size distribution analysis unit 171, the epidermis shape distribution analysis unit 172, and the epidermis shape distribution analysis unit 173 of the acquired element analysis unit 123.

Referring back to FIG. 5, in step S4, the acquired element analysis unit 123 performs the acquired element analysis process.

[Acquired Element Analysis Process]

Figure 9:
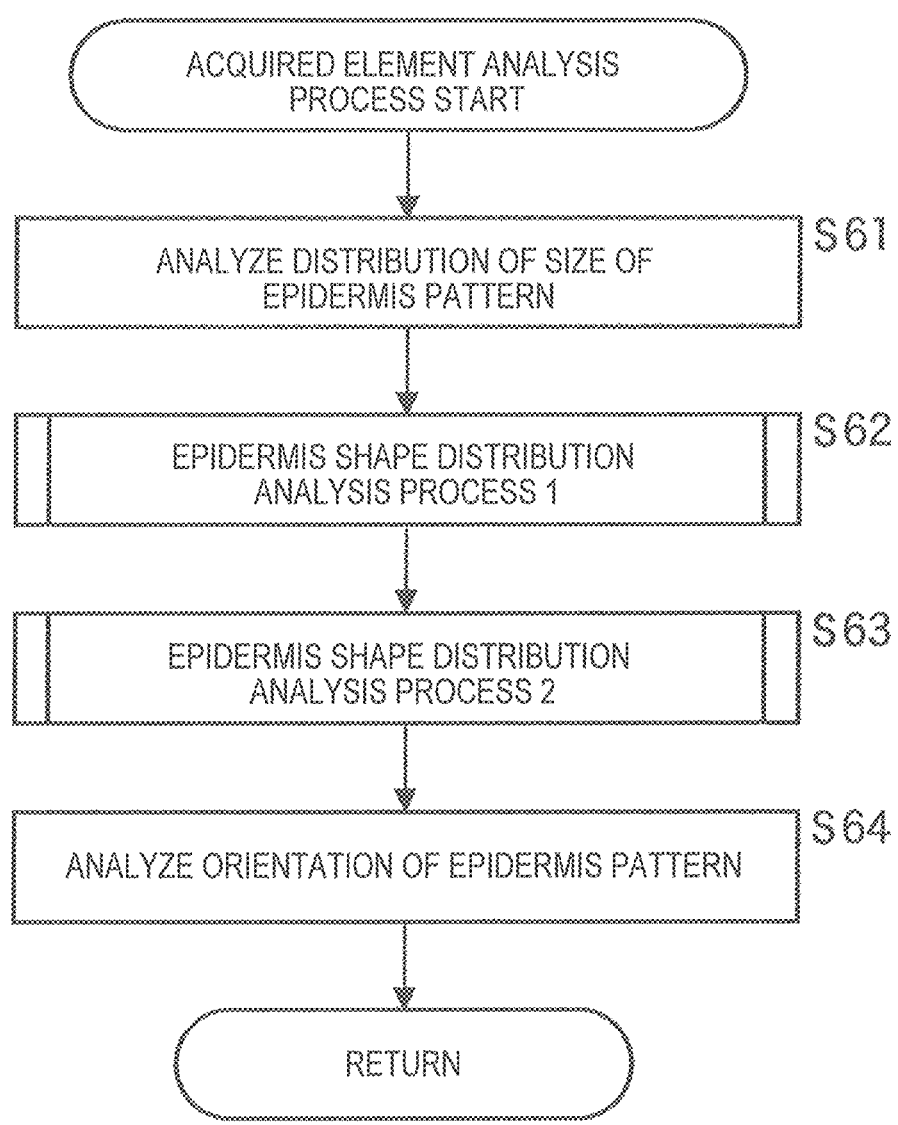
FIG. 9 is a flow chart illustrating an acquired element analysis process.

Here, details of the acquired element analysis process will be described with reference to the flow chart shown in FIG. 9.

In step S61, the epidermis size distribution analysis unit 171 analyzes the distribution of sizes of the epidermis patterns.

Figure 10:
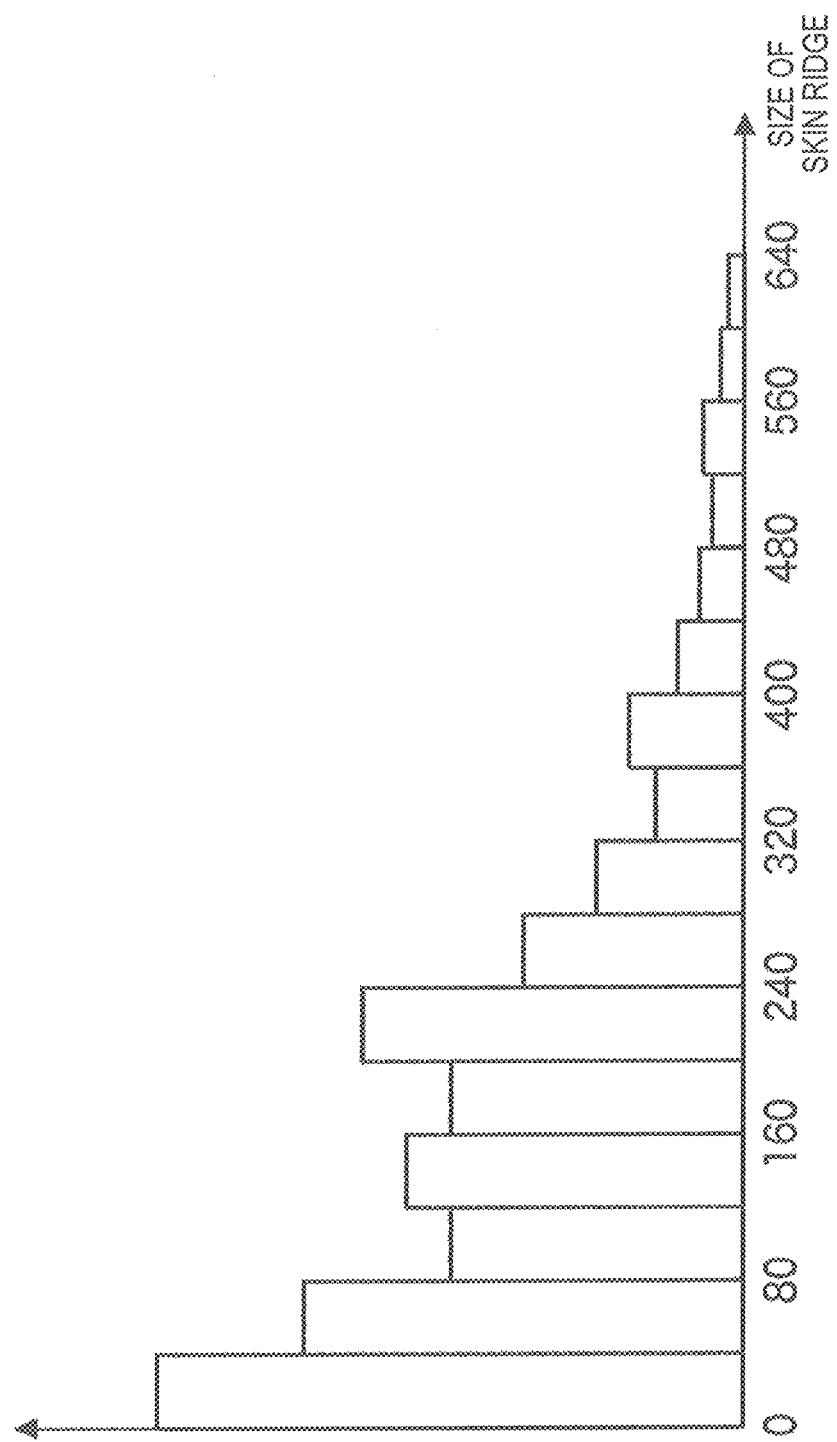
FIG. 10 is a diagram illustrating an example of a histogram of sizes of skin ridge regions.

In particular, first, the epidermis size distribution analysis unit 171 creates a histogram of sizes of the skin ridge regions. FIG. 10 illustrates an example of the histogram of sizes (areas) of the skin ridge regions. The horizontal axis and the vertical axis indicate the sizes of the skin ridge regions and the frequency $frq_n$ of each bin of the histogram in FIG. 10, respectively.

Next, the epidermis size distribution analysis unit 171 calculates the average value $H_{avg}$ of sizes of the skin ridge regions by means of Equation 2 below.

$$H_{avg} = \frac{\sum_n (n \cdot frq_n)}{\sum_n (frq_n)} \quad (2)$$

In addition, n indicates a median value of each bin.

In addition, the epidermis size distribution analysis unit 171 calculates the variance $H_{var}$ of sizes of the skin ridge regions by means of Equation 3 below.

$$H_{var} = \frac{\sum_n ((n - H_{avg})^2 \cdot frq_n)}{\sum_n (frq_n)} \quad (3)$$

Figure 11:
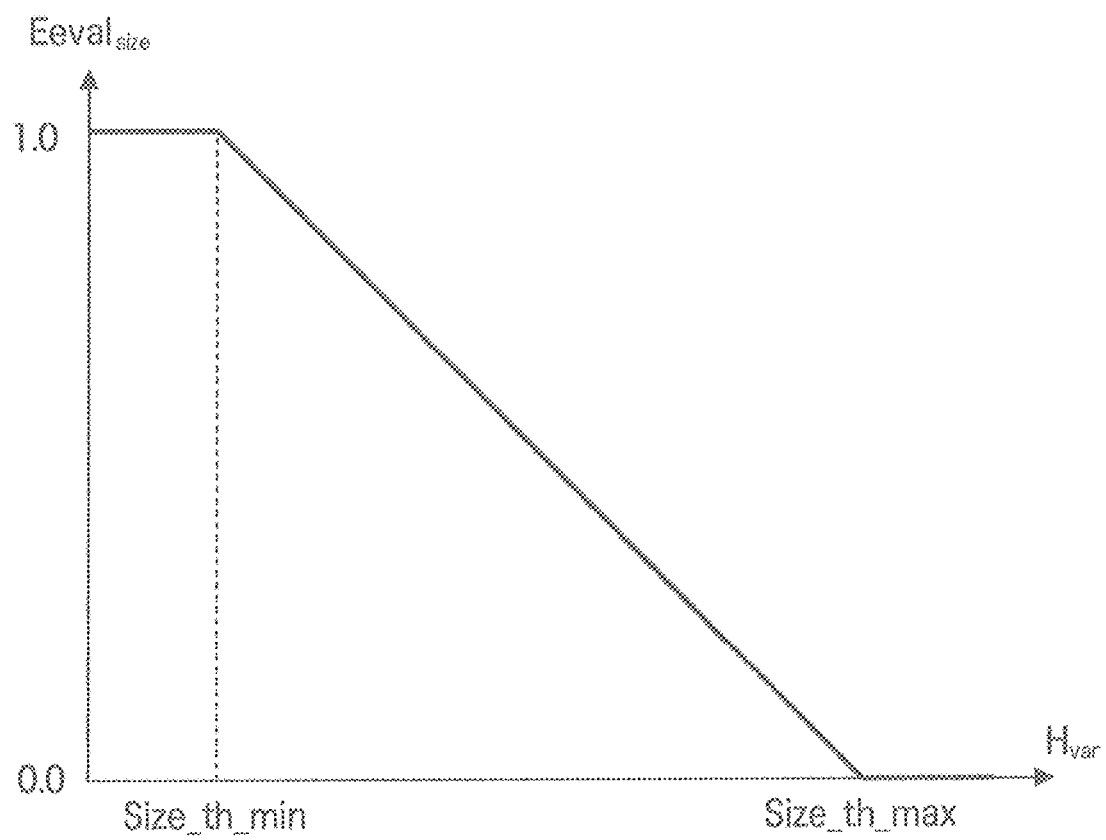
FIG. 11 is a diagram illustrating an example of a normalization curve for calculating evaluation values of epidermis size distribution.

Further, the epidermis size distribution analysis unit 171 calculates the evaluation value of the epidermis size distribution Eeval$_{size}$ in which the variance $H_{var}$ is normalized within a range of 0 to 1 by means of the normalization curve shown in FIG. 11. Here, each of Size_th_min and Size_th_max is threshold values that determine the normalization curve in FIG. 11.

The evaluation value of the epidermis size distribution Eeval$_{size}$ increases as the variance of sizes of the skin ridge regions $H_{var}$ decreases. That is, the evaluation value of the epidermis size distribution Eeval$_{size}$ increases as the variation in size of the skin ridge regions decreases. Accordingly, the evaluation value of the epidermis size distribution Eeval$_{size}$ becomes the index for indicating the uniformity of sizes of the skin ridge regions.

The epidermis size distribution analysis unit 171 supplies the evaluation value of the epidermis size distribution Eeval$_{size}$ to the texture evaluation unit 124.

In step S62, the epidermis shape distribution analysis unit 172 performs the epidermis shape distribution analysis process 1.

[Epidermis Shape Distribution Analysis Process 1]

Figure 12:
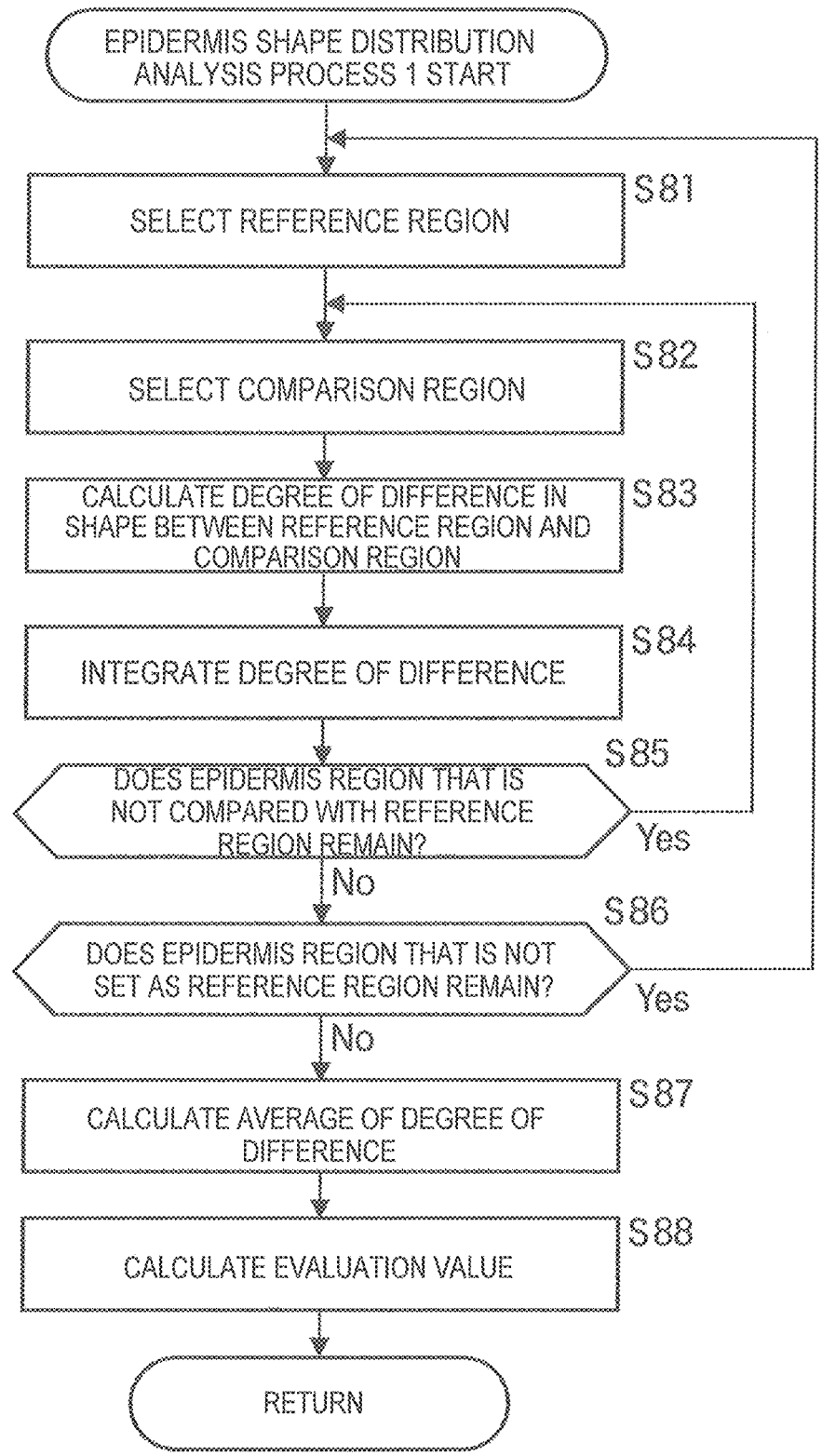
FIG. 12 is a flow chart illustrating epidermis shape distribution analysis process 1.

Here, details of the epidermis shape distribution analysis process 1 of step S62 will be described with reference to the flow chart in FIG. 12.

In step S81, the epidermis shape distribution analysis unit 172 selects a reference region. That is, the epidermis shape distribution analysis unit 172 selects one skin ridge region that is not yet set as the reference region, and then sets the one skin ridge region as the reference region.

In step S82, the epidermis shape distribution analysis unit 172 selects a comparison region. That is, the epidermis shape distribution analysis unit 172 selects one skin ridge region that is not used for comparison with the shape of the reference region, and then sets the one skin ridge region as the comparison region.

In step S83, the epidermis shape distribution analysis unit 172 calculates the degree of difference in shape between the reference region and the comparison region.

For example, the epidermis shape distribution analysis unit 172 quantifies the shapes of the reference region and the comparison region using the Hu moment invariant, and calculates the degree of difference in shape between the reference region and the comparison region based on the quantified values.

Here, the Hu moment invariant will be described briefly.

First, the image moment $M_{pq}$ indicating variance values of pixels where an origin point of the image is centered is calculated as in Equation 4 below.

$$M_{pq} = \sum_{x,y} (I(x, y) \cdot x^p \cdot y^q) \quad (4)$$

The image moment $M_{pq}$ increases as higher pixel values scatter in locations farther away from the origin point.

In addition, p and q in Equation 4 indicate weights in the X-axis and Y-axis directions, respectively. Accordingly, the weight on the variance toward the X-axis direction increases when the value p increases, and the weight on the variance toward the Y-axis direction increases when the value q increases.

Next, the central moment (centroid moment) $\mu_{pq}$ indicating the variance where centroids in the X-axis and Y-axis directions are taken into consideration in the pixel values within the image is calculated as in Equation 5 below.

$$\mu_{pq} = \sum_{x,y} (I(x, y) \cdot (x - x_c)^p \cdot (y - y_c)^q) \quad (5)$$

Here, $x_c$ and $y_c$ are expressed as Equations (6a) and (6b) below, and indicate centroid positions in the X-axis and Y-axis directions, respectively.

$$x_c = M_{10}/M_{00} \quad (6a)$$

$$y_c = M_{01}/M_{00} \quad (6b)$$

Finally, by normalizing the central moment $\mu_{pq}$ using the image moment $M_{pq}$ in Equation 7, the normalized centroid moment $\eta_{pq}$ is obtained.

$$\eta_{pq} = \mu_{pq}/M_{00}^{((p+q)/2+1)} \quad (7)$$

Since this normalization prevents the spreading state of the variance from affecting the moment value, the normalized centroid moment $\eta_{pq}$ becomes invariant with respect to the parallel movement or rotational movement of an object within the image or image sizes.

The Hu moment invariant is a combination of the normalized centroid moments $\eta_{pq}$, and is defined as Equations (8a) to (8g) below.

$$h_1 = \eta_{20} + \eta_{02} \quad (8a)$$

$$h_1 = (\eta_{20} - \eta_{02})^2 + 4\eta_{11}^2 \quad (8b)$$

$$h_3 = (\eta_{30} - 3\eta_{12})^2 + (3\eta_{21} - \eta_{03})^2 \quad (8c)$$

$$h_4 = (\eta_{30} + \eta_{12})^2 + (\eta_{21} + \eta_{03})^2 \quad (8d)$$

$$h_5 = (\eta_{30} - 3\eta_{12})(\eta_{30} + \eta_{12})[(\eta_{30} + \eta_{12})^2 - 3(\eta_{21} + \eta_{03})^2] + (3\eta_{21} - \eta_{03})(\eta_{21} + \eta_{03})[3(\eta_{30} + \eta_{12})^2 - (\eta_{21} + \eta_{03})^2] \quad (8e)$$

$$h_6 = (\eta_{20} - \eta_{03})[(\eta_{30} + \eta_{12})^2 - (\eta_{21} + \eta_{03})^2] + 4\eta_{11}(\eta_{30} + \eta_{12})(\eta_{21} + \eta_{03}) \quad (8f)$$

$$h_7 = (3\eta_{21} - \eta_{03})(\eta_{12} + \eta_{03})[3(\eta_{30} + \eta_{12})^2 - (\eta_{21} + \eta_{03})^2] - (\eta_{30} - 3\eta_{12})(\eta_{21} + \eta_{03})[3(\eta_{30} + \eta_{12})^2 - (\eta_{21} + \eta_{03})^2] \quad (8g)$$

In addition, details of the Hu moment invariant are disclosed, for example, in M-K. Hu. "Visual pattern recognition by moment invariants," IRE Transaction on Information Theory, February, 1962, Volume 8, pp. 179-187.

The epidermis shape distribution analysis unit 172 calculates the Hu moment amount $h^A_i$ of the reference region and the Hu moment amount $h^B_i$ of the comparison region based on Equations (4) to (8g). However, in Equations (4) and (5), pixel values $I_{bin}(x,y)$ of the binarized epidermis image are used instead of the pixel values I(x,y).

The epidermis shape distribution analysis unit 172 calculates the degree of difference D(A,B) in shape between the reference region (region A) and the comparison region (region B) by means of Equation (9a).

$$D(A, B) = \sum_{i=1}^{7} \left| \frac{1}{m_i^A} - \frac{1}{m_i^B} \right| \quad (9a)$$

Here, $m^A_i$ and $m^B_i$ indicate amounts represented by Equation (10) below.

$$m^A_i = \text{sign}(h^A_i) \cdot \log(h^A_i)$$

$$m^B_i = \text{sign}(h^B_i) \cdot \log(h^B_i) \quad (10)$$

In addition, the degree of difference D(A,B) may be calculated by Equation (9b) or (9c) instead of Equation (9a).

$$D(A, B) = \sum_{i=1}^{7} |m_i^A - m_i^B| \quad (9b)$$

$$D(A, B) = \sum_{i=1}^{7} \left| \frac{|m_i^A - m_i^B|}{m_i^A} \right| \quad (9c)$$

The degree of difference D(A,B) of any of Equations (9a) to (9c) also decreases when shapes of the reference region and the comparison region become closer to each other.

In step S84, the epidermis shape distribution analysis unit 172 integrates the degrees of difference. That is, the epidermis shape distribution analysis unit 172 adds the newly calculated degree of difference to the integrated value of the degrees of difference of every skin ridge region so far.

In step S85, the epidermis shape distribution analysis unit 172 determines whether or not skin ridge regions that are not compared with the reference region remain. When it is determined that skin ridge regions not compared with the reference region remain, the process returns to step S82.

Thereafter, in step S85, a process from step S82 to step S85 is repeatedly carried out until it is determined that no skin ridge regions not compared with the reference region remain.

Meanwhile, in step S85, when it is determined that no skin ridge regions not compared with the reference region remain, the process proceeds to step S86.

In step S86, the epidermis shape distribution analysis unit 172 determines whether or not a skin ridge region that is not set as the reference region remains. When it is determined that a skin ridge region that is not set as the reference region remains, the process returns to step S81.

Thereafter, in step S86, a process from steps S81 to S86 is repeatedly carried out until it is determined that no skin ridge region that is not set as the reference region remains. Accordingly, the degree of difference is calculated for all combination of the skin ridge regions, and the accumulative added value of the degrees of difference is also calculated.

Meanwhile, in step S86, when it is determined that no skin ridge region that is not set as the reference region remains, the process proceeds to step S87.

In step S87, the epidermis shape distribution analysis unit 172 calculates the average of degrees of difference $\text{Diff}_{avg}$ by means of Equation (11) below.

$$\text{Diff}_{avg} = \frac{\sum_{i=0}^{N_{ridge}-1} \sum_{j=i+1}^{N_{ridge}-1} D(R_i, R_j)}{N_{comp}} \quad (11)$$

In addition, $R_i$ and $R_j$ indicate skin ridge regions of the labels i and j, respectively. Accordingly, the denominator of the right side of Equation 11 is the accumulative added value of the degrees of difference in shape for all combinations of the skin ridge regions. In addition, $N_{comp}$ indicates the number of comparisons of shapes of the skin ridge regions, which is obtained by Equation 12 below.

$$N_{comp} = \frac{N_{ridge}(N_{ridge} - 1)}{2} \quad (12)$$

In step S88, the epidermis shape distribution analysis unit 172 calculates the evaluation value. In particular, the epidermis shape distribution analysis unit 172 calculates the evaluation value of the epidermis shape distribution $\text{Eeval}_{shape}$ in which the average of the degrees of difference $\text{Diff}_{avg}$ is normalized within a range of 0 to 1 by means of the normalization curve shown in FIG. 13. Here, Shape_th_min and Shape_th_max are threshold values that determine the normalization curve in FIG. 13, respectively.

The evaluation value of the epidermis shape distribution $\text{Eeval}_{shape}$ increases as the average of degrees of difference $\text{Diff}_{avg}$ in shape between the skin ridge regions decreases. That is, the evaluation value of the epidermis shape distribution $\text{Eeval}_{shape}$ increases as the variation in shape between the skin ridge regions decreases. Accordingly, the evaluation value of the epidermis shape distribution $\text{Eeval}_{shape}$ becomes the index for indicating the uniformity of shapes of the skin ridge regions.

The epidermis shape distribution analysis unit 172 supplies the evaluation value of the epidermis shape distribution $\text{Eeval}_{shape}$ to the texture evaluation unit 124.

Thereafter, the epidermis shape distribution analysis process 1 is finished.

Referring back to FIG. 9, in step S63, the epidermis shape distribution analysis unit 173 performs the epidermis shape distribution analysis process 2.

[Epidermis Shape Distribution Analysis Process 2]

Here, details of the epidermis shape distribution analysis process 2 in step S63 will be described with reference to the flow chart shown in FIG. 14.

In step S101, the epidermis shape distribution analysis unit 173 selects a reference shape.

It is ideal for the shape of the skin ridge to usually be a triangle or a rhombus. On the other hand, a shape such as a bifurcated shape or elongated shape is not considered to be ideal.

The epidermis shape distribution analysis unit 173, for example, sets Shape0 to Shape3 shown in FIG. 15 as the reference shapes. The reference shapes Shape0 and Shape1 are a triangle and a rhombus and are close to ideal shapes of the skin ridges, respectively. On the other hand, the reference shapes Shape2 and Shape3 are bifurcated and elongated shapes and are close to the shapes of the skin ridges that are not ideal, respectively.

The epidermis shape distribution analysis unit 173 selects one reference shape that is not yet compared with the skin ridge regions.

In step S102, the epidermis shape distribution analysis unit 173 selects a comparison region. That is, the epidermis shape distribution analysis unit 173 selects one skin ridge region that is not yet compared with the reference region, and sets the selected skin ridge region as the comparison region.

In step S103, the epidermis shape distribution analysis unit 173 calculates the degree of difference in shape between the reference shape and the shape of the comparison region. In addition, to this calculation of the degree of difference, the same method as that of calculating the degree of difference between the comparison region and the reference region of the skin ridge regions in step S83 of FIG. 12 described above is applied.

In step S104, the epidermis shape distribution analysis unit 173 integrates the degrees of difference. That is, the epidermis shape distribution analysis unit 173 adds the newly calculated degree of difference to the integrated value of the degrees of difference between the current reference shape and each of the skin region regions so far.

In step S105, the epidermis shape distribution analysis unit 173 determines whether or not a skin ridge region not compared with the current reference shape remains. When it is determined that a skin ridge region not compared with the current reference shape remains, the process returns to step S102.

Thereafter, in step S105, the process from steps S102 to S105 is repeatedly carried out until it is determined that that no skin ridge region not compared with the current reference shape remains.

On the other hand, in step S105, when it is determined that no skin ridge region not compared with the current reference shape remains, the process proceeds to step S106.

In step S106, the epidermis shape distribution analysis unit 173 determines whether or not a reference shape that is not compared remains. When it is determined that a reference shape that is not compared remains, the process returns to step S101.

Thereafter, in step S106, a process from steps S101 to S106 is repeatedly carried out until it is determined that no reference shape that is not compared remains. Accordingly, as shown in Equation 13, the accumulative added value $\text{Diff}_I$ of the degrees of difference in shape between each of the reference shapes and each of the skin ridge regions is calculated.

$$\text{Diff}_i = \sum_{j=0}^{N_{ridge}} D(S_i, R_j) \quad (13)$$

In addition, $S_i$ indicates the reference shape having the value i of ID.

On the other hand, in step S106, when it is determined that no reference shape that is not compared remains, the process proceeds to step S107.

In step S107, the epidermis shape distribution analysis unit 173 calculates the ratio of shapes of the skin ridge regions. In particular, the epidermis shape distribution analysis unit 173 calculates the epidermis shape distribution information ShapeRatio$_i$ indicating the ratio of shapes of the skin ridge regions by means of Equation 14.

$$ShapeRatio_i = \frac{Diff_i}{\sum_{i=0}^{N_{RS}-1} Diff_i} \quad (14)$$

Here, $N_{RS}$ indicates the total number of reference shapes.

Accordingly, the epidermis shape distribution information ShapeRatio$_i$ indicates the ratio of the skin ridge regions having the shapes close to the reference shape of which the ID has the value i.

The epidermis shape distribution analysis unit 173 supplies the epidermis shape distribution information ShapeRatio$_i$ to the texture evaluation unit 124.

Thereafter, the epidermis shape distribution analysis process 2 is finished.

Referring back to FIG. 9, in step S64, the epidermis orientation analysis unit 174 analyzes the orientation of the epidermis patterns.

In particular, the four-directional filtering unit 181 of the epidermis orientation analysis unit 174, for example, applies each of the four-directional filters $f_0$ to $f_3$ shown in Equations (15a) to (15d) to the noise-removed epidermis image as shown in Equation 16.

$$f_0 = \begin{pmatrix} 1 & 0 & -1 \\ 1 & 0 & -1 \\ 1 & 0 & -1 \end{pmatrix} \quad (15a)$$

$$f_1 = \begin{pmatrix} 0 & 1 & 1 \\ -1 & 0 & 1 \\ -1 & -1 & 0 \end{pmatrix} \quad (15b)$$

$$f_2 = \begin{pmatrix} 1 & 1 & 1 \\ 0 & 0 & 0 \\ -1 & -1 & -1 \end{pmatrix} \quad (15c)$$

$$f_3 = \begin{pmatrix} 1 & 1 & 0 \\ 1 & 0 & -1 \\ 0 & -1 & -1 \end{pmatrix} \quad (15d)$$

$$I_{HPFi} = f_i \otimes I_{LPF} \quad (16)$$

In addition, the filter $f_0$, the filter $f_1$, the filter $f_2$, and the filter $f_3$ are edge extraction filters of 0° (horizontal direction), 45°, 90° (vertical direction), and 135°, respectively. In addition, $I_{LPF}$ indicates the noise-removed epidermis image, and $I_{HPFi}$ indicates the filter output image obtained by applying the filter $f_i$ to the noise-removed epidermis image $I_{LPF}$.

The four-directional filtering unit 181 supplies the filter output image $I_{HPFi}$ to the absolute value sum calculation unit 182.

Next, the absolute value sum calculation unit 182 calculates the sum of absolute values $S_i$ of the pixel values $I_{HPFi}(x,y)$ within the image in each filter output image by means of Equation 17.

$$S_i = \sum_{x,y} |I_{HPFi}(x,y)| \quad (17)$$

The absolute value sum calculation unit 182 supplies the obtained sum of absolute values $S_i$ to the addition unit 183 and the division unit 184.

The addition unit 183 integrates the sums of absolute values $S_i$, and supplies the obtained integrated value $\Sigma s_i$ to the division unit 184.

The division unit 184 divides each of the sums of absolute values $S_i$ by the integrated value $\Sigma s_i$, and supplies the obtained value $s_i/\Sigma s_i$ to the evaluation value calculation unit 185.

The evaluation value calculation unit 185 calculates the evaluation value of the epidermis orientation Eeval$_{direction}$ by means of Equation 18 below.

$$Eeval_{direction} = \prod_i \exp\left(-gain \cdot \left|\frac{s_i}{\sum_i s_i} - \frac{1}{4}\right|\right) \quad (18)$$

In addition, gain is a gain value and is set as a predetermined value.

Here, when edge directions of the skin ridge regions are uniformly distributed in four directions such as vertical, horizontal and sloped directions (0°, 45°, 90°, and 135°), each si/Σsi is ¼, and the evaluation value of the epidermis orientation Eeval$_{direction}$ is 1. On the other hand, when the edge directions of the skin ridge regions are not uniformly distributed in the four directions, at least one of si/Σsi is not ¼, so that the evaluation value of the epidermis orientation Eeval$_{direction}$ is smaller than 1. Accordingly, the evaluation value of the epidermis orientation Eeval$_{direction}$ becomes the index for indicating the uniformity of distribution in the edge directions of the skin ridge regions.

The evaluation value calculation unit 185 supplies the evaluation value of the epidermis orientation Eeval$_{direction}$ to the texture evaluation unit 124.

Thereafter, the acquired element analysis process is finished.

Referring back to FIG. 5, in step S5, the texture evaluation unit 124 calculates the texture evaluation value.

For example, the texture evaluation unit 124 calculates the texture evaluation value eval1$_{total}$ by means of Equation 19 below.

$$eval1_{total} = Eeval_{size} \times Eeval_{shape} \times Eeval_{direction} \quad (19)$$

The texture evaluation value eval1$_{total}$ increases when each of the uniformity of sizes of the skin ridges, the uniformity of shapes of the skin ridges, and the uniformity of distribution of the skin ridge orientations increases, that is, when the textures are generally good (when the texture uniformity is high). In addition, the uniformity of sizes of the skin ridges, the uniformity of shapes of the skin ridges, and the uniformity of distribution of the skin ridge orientations are changed in an acquired manner by aging, health, skin care and so forth. Accordingly, the texture evaluation value eval1$_{total}$ becomes the index for evaluating the uniformity of skin textures that are changed in an acquired manner.

The uniformity of textures greatly influences the aesthetic view of skin as the fineness of the texture does. That is, the appearance of the skin is worse when the textures are not generally good even when the textures are fine, whereas the appearance of the skin is better when the textures are generally good even when the textures are not fine.

In addition, instead of the texture evaluation value $eval1_{total}$, or along with the texture evaluation value $eval1_{total}$, the texture evaluation value $eval2_{total}$ may be calculated as in Equation 20 below.

$$eval2_{total} = Eeval_{size} \times Eeval_{shape} \times Eeval_{direction} \times ShapeRatio_{ideal} \quad (20)$$

$ShapeRatio_{ideal}$, for example, is calculated as in Equation (21) below.

$$ShapeRatio_{ideal} = ShapeRatio_0 \times ShapeRatio_1 \quad (21)$$

$ShapeRatio_0$ is the ShapeRatio with respect to the reference shape Shape0 of the triangle in FIG. 15, and $ShapeRatio_1$ is the ShapeRatio with respect to the reference shape Shape1 of the rhombus in FIG. 15. That is, $ShapeRatio_{ideal}$ indicates the ratio at which the skin ridge regions have the ideal shape such as a triangle or a rhombus.

Accordingly, in addition to the uniformity of textures, the texture evaluation value $eval2_{total}$ increases when the ratio of skin ridges having the ideal shapes increases. Thus, the texture evaluation value $eval2_{total}$ becomes an index that is compared with the texture evaluation value $eval1_{total}$ to evaluate the acquired elements that affect the texture state of the skin in further detail.

The texture evaluation unit 124 supplies the evaluation result of the texture state of the skin to the evaluation result presentation unit 125. Here, the texture evaluation unit 124 supplies not only the texture evaluation values $eval1_{total}$ and $eval2_{total}$ but also each evaluation value used for calculating the texture evaluation values $eval1_{total}$ and $eval2_{total}$ to the evaluation result presentation unit 125.

In step S6, the evaluation result presentation unit 125 presents the evaluation result. In addition, with respect to specific examples of the method of presenting the evaluation result, the second embodiment of the present technology will be described.

Thereafter, the texture evaluation process is finished.

As described above, based on the uniformity of textures, which is an acquired element indicating the texture state of the skin, and the shapes of skin ridges, it is possible to evaluate the texture state of the skin. As a result, it is possible to more correctly evaluate the texture state of the skin.

2. Second Embodiment

Next, the second embodiment of the present technology will be described with reference to FIGS. 16 to 23. In the second embodiment, not only the acquired elements but also the inherent elements are analyzed to evaluate the texture state of the skin.

[Configuration Example of Image Processing System 201]

Figure 16:
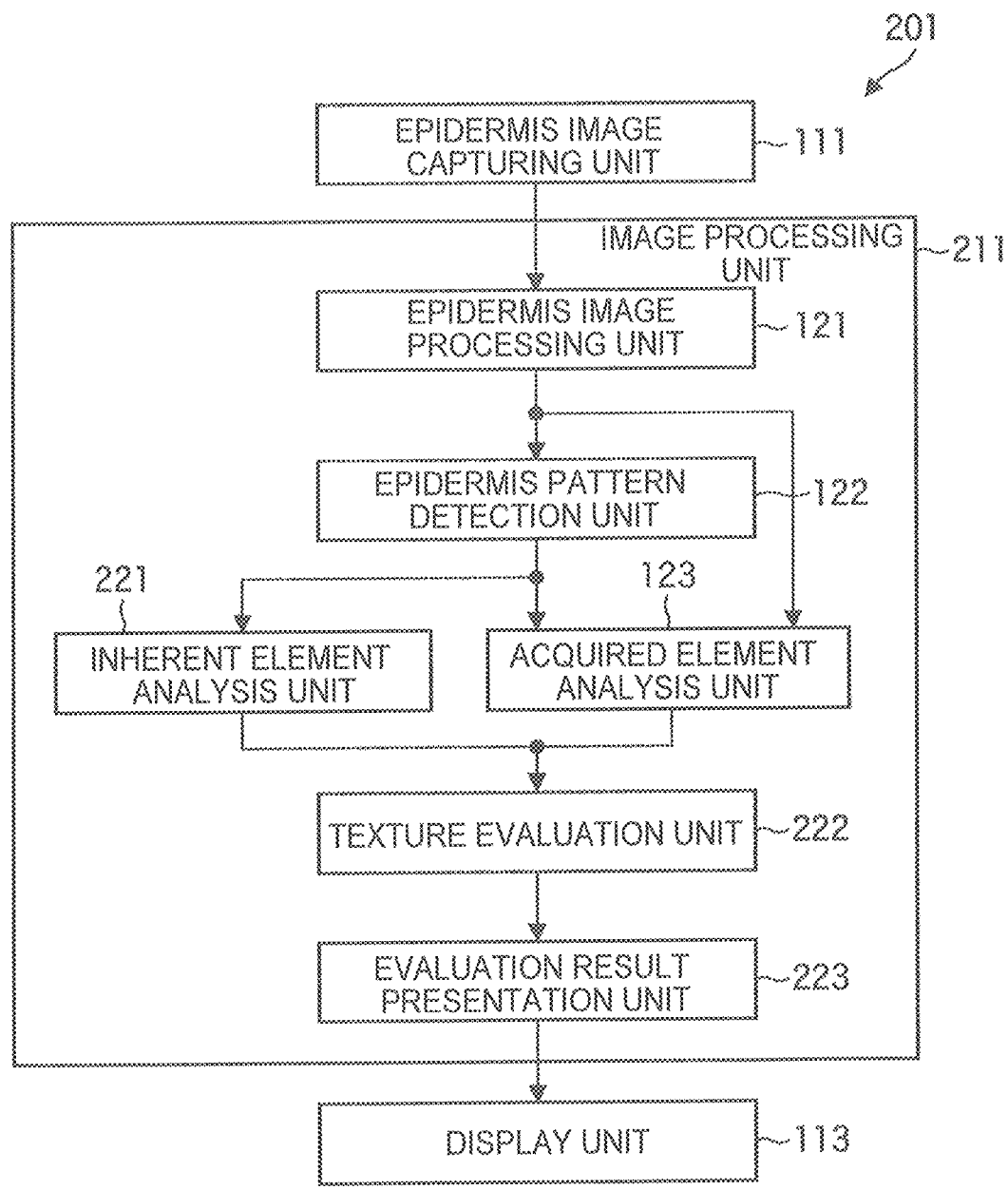
FIG. 16 is a block diagram illustrating an image processing system in accordance with a second embodiment of the present technology.

FIG. 16 is a block diagram illustrating the configuration example of the image processing system 201 in accordance with the second embodiment of the present technology. In addition, like parts corresponding to those in FIG. 1 are designated by like numerals. With respect to parts to be processed in the same manner, the repeated description thereof is properly omitted.

The image processing system 201 differs from the image processing system 101 of FIG. 1 in that the image processing unit 211 is disposed instead of the image processing unit 112. In addition, the image processing unit 211 differs from the image processing unit 112 in that the inherent element analysis unit 221 is additionally disposed and the texture evaluation unit 222 and the evaluation result presentation unit 223 are disposed instead of the texture evaluation unit 124 and the evaluation result presentation unit 125.

The inherent element analysis unit 221, as will be described later, performs the inherent element analysis on the inherent elements among elements indicating the texture state of the skin based on the detection result of the epidermis patterns. The inherent element analysis unit 221 supplies the analysis result to the texture evaluation unit 222.

The texture evaluation unit 222 evaluates the texture state of the skin of the evaluation target based on the analysis result from the acquired element analysis unit 123 and the analysis result from the inherent element analysis unit 221, and supplies the evaluation result to the evaluation result presentation unit 223.

The evaluation result presentation unit 223 causes the display unit 113 to display the information indicating the evaluation result of the texture state of the skin of the evaluation target.

[Configuration Example of Inherent Element Analysis Unit 221]

Figure 17:
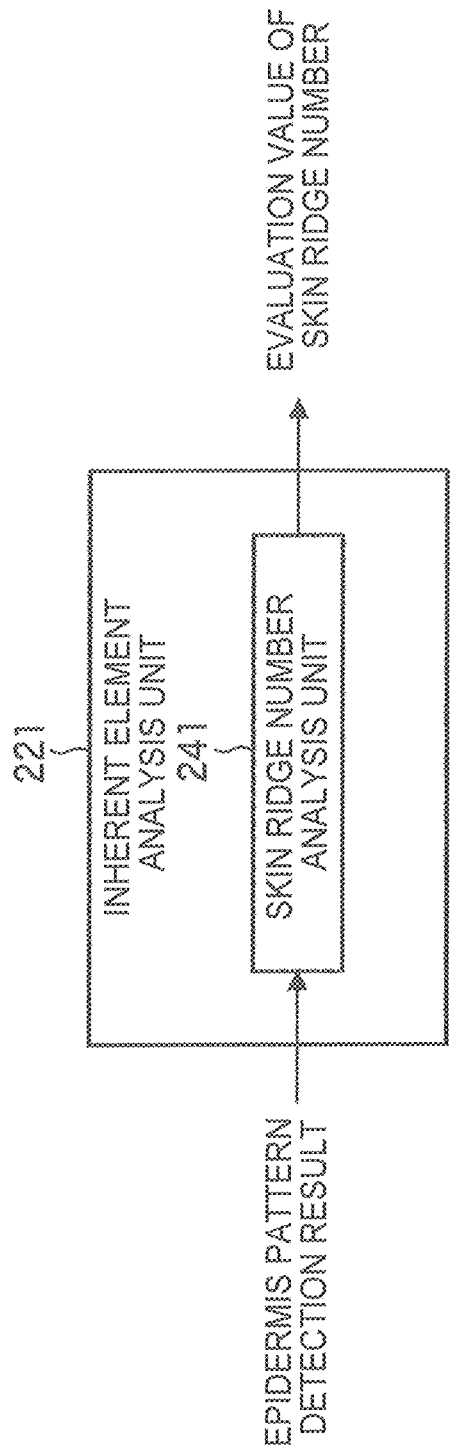
FIG. 17 is a block diagram illustrating a configuration example of an inherent element analysis unit.

FIG. 17 is a block diagram illustrating the configuration example of the inherent element analysis unit 221.

The inherent element analysis unit 221 includes a skin ridge number analysis unit 241.

The skin ridge number analysis unit 241 obtains the detection result of the epidermis patterns from the labeling process unit 152 of the epidermis pattern detection unit 122. The skin ridge number analysis unit 241 then calculates the evaluation value of the number of skin ridges that is the index for indicating the fineness of the skin texture, based on the number of skin ridges $N_{ridge}$ included in the detection result of the epidermis patterns. The skin ridge number analysis unit 241 supplies the calculated evaluation value of the number of skin ridges to the texture evaluation unit 222.

In addition, it is known that the number of skin ridges $N_{ridge}$ is inherent and that variation due to aging, health, skin care and so forth is small. Accordingly, the evaluation value of the number of skin ridges becomes the index for evaluating the inherent property of the texture state of the skin.

[Texture Evaluation Process]

Next, the texture evaluation process carried out by the image processing system 201 will be described with reference to the flow chart of FIG. 18.

In addition, this process, for example, is initiated when the instruction to execute the texture evaluation process is input through an input unit not shown in the image processing system 201.

Figure 5:
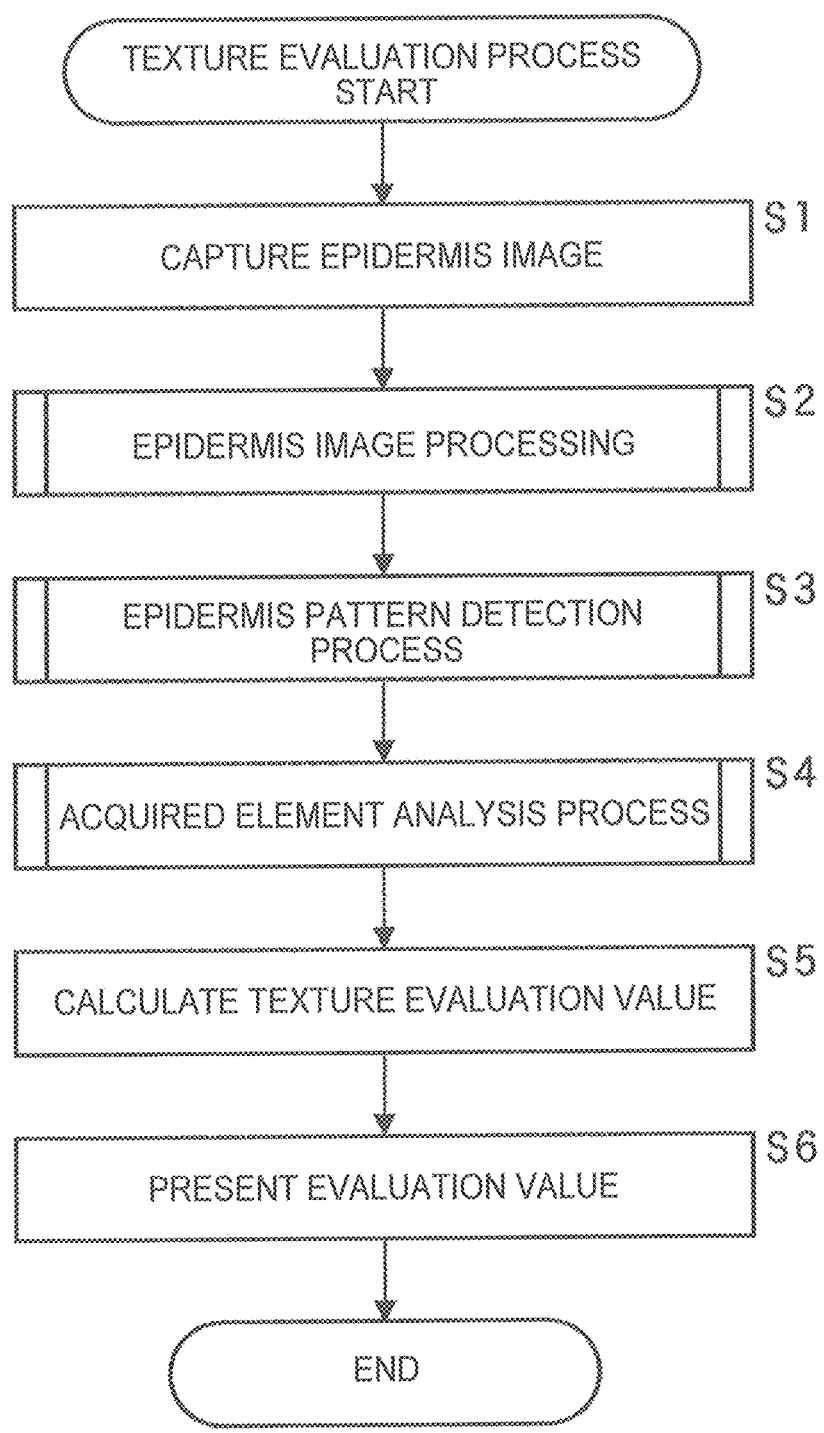
FIG. 5 is a flow chart illustrating a texture evaluation process.

Processing from step S201 to step S204 is same as that from step S1 to step S4 of FIG. 5, and the repeated description thereof is omitted.

In step S205, the inherent element analysis unit 221 performs the inherent element analysis process.

[Inherent Element Analysis Process]

Here, details of the inherent element analysis process will be described with reference to the flow chart of FIG. 19.

In step S221, the skin ridge number analysis unit 241 of the inherent element analysis unit 221 analyzes the number of skin ridges. In particular, the skin ridge number analysis unit 241 calculates the evaluation value of the number of skin ridges $Eeval_{num}$ that the number of skin ridges $N_{ridge}$ are detected by the labeling process unit 152 of the epidermis pattern detection unit 122 and are normalized within a range of 0 to 1 by the normalization curve shown in FIG. 20. Here, each of Num_th_min and Num_th_max is threshold values that determine the normalization curve in FIG. 20.

The evaluation value of the number of skin ridges $Eeval_{num}$ increases when the number of skin ridges $N_{ridge}$ increases. In addition, since the number of skin ridges $N_{ridge}$ indicates the number of skin ridges within the epidermis image (i.e., the number of skin ridges per unit area), it may be said that the texture of the skin is finer when the number of skin ridges $N_{ridge}$ increases. Accordingly, the evaluation value of the number of skin ridges $Eeval_{num}$ becomes an index indicating the fineness of the skin.

The skin ridge number analysis unit 241 supplies the evaluation value of the skin ridges $Eeval_{num}$ to the texture evaluation unit 222.

Thereafter, the inherent element analysis process is finished.

Referring back to FIG. 18, in step S206, the texture evaluation unit 222 calculates the texture evaluation value.

For example, the texture evaluation unit 222 calculates the texture evaluation value $eval3_{total}$ by means of Equation (22) below.

$$eval3_{total} = \alpha_{inherent} \times Eeval_{num} + (1-\alpha_{inherent}) \times eval1_{total} \quad (22)$$

In addition, $\alpha_{inherent}$ is the weight indicating the ratio at which the inherent element affects the texture state of the skin, and is set within a range of 0 to 1. In addition, it is preferable that such weight $\alpha_{inherent}$ be automatically set to a proper value in accordance with elements estimated to affect the texture state such as sex, race, and age, for example.

In addition, the texture evaluation value $eval1_{total}$ of Equation (22) is calculated based on Equation (19) as described above.

The texture evaluation value $eval3_{total}$ is one in which not only the acquired element property of the texture state of the skin but also the inherent property such as texture fineness is evaluated. Accordingly, the texture evaluation value $eval3_{total}$ becomes the index that is compared with the texture evaluation value $eval1_{total}$ to evaluate the texture state of the skin in further detail.

In addition, in Equation (22), the texture evaluation value $eval1_{total}$ of Equation (20) may be used instead of the texture evaluation value $eval1_{total}$.

The texture evaluation unit 222 supplies the evaluation result of the texture state of the skin to the evaluation result presentation unit 223. Here, the texture evaluation unit 222 supplies not only the texture evaluation value $eval3_{total}$ but also each evaluation value used for calculating the texture evaluation value $eval3_{total}$ to the evaluation result presentation unit 223.

In step S207, the evaluation result presentation unit 223 presents the evaluation result.

Figure 21:
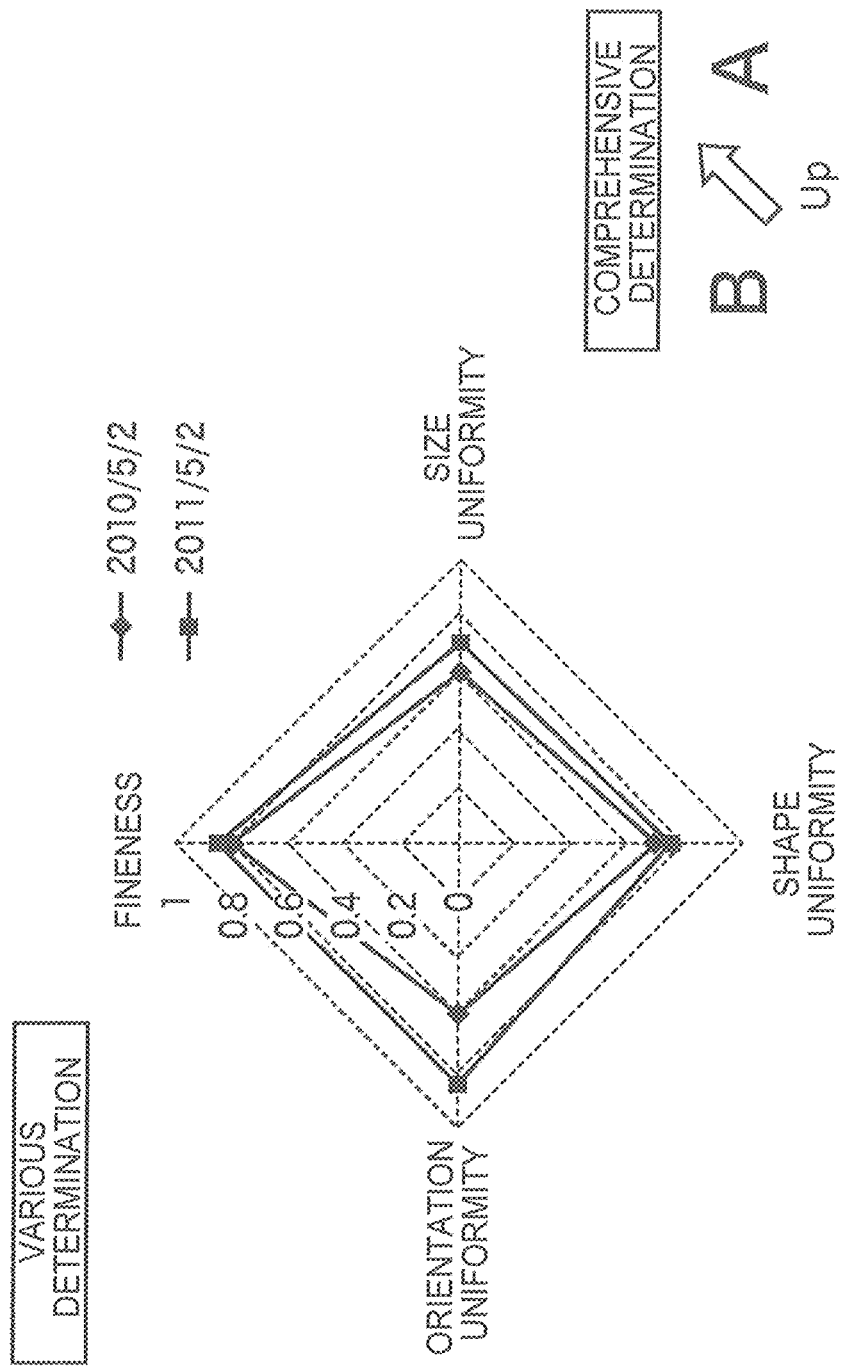
FIG. 21 is a diagram illustrating an example of a screen presenting evaluation results of the texture state of the skin.

For example, the evaluation result presentation unit 223 causes the display unit 113 to display the screen shown in FIG. 21. In the present example, a radar chart that individually compares the uniformity of sizes of the skin ridges previous and current times, the uniformity of shapes of the skin ridges previous and current times, the uniformity of distribution of the skin ridge orientations previous and current times, and the evaluation values of fineness of the texture previous and current times is illustrated. The evaluation value of the epidermis size distribution $Eeval_{size}$, the evaluation value of the epidermis shape distribution $Eeval_{shape}$, the evaluation value of the epidermis orientation $Eeval_{direction}$, and the evaluation value of the number of skin ridges $Eeval_{num}$ are used as the values of the radar chart.

In addition, in the present example, the change in comprehensive determination of the texture states of the skin previous and current times is shown. Such a comprehensive determination value is determined, for example, based on the texture evaluation value $eval3_{total}$ using ing the table shown in FIG. 22. That is, the comprehensive determination value is given with a higher evaluation value when the texture evaluation value $eval3_{total}$ increases.

Accordingly, the evaluation target may recognize the texture state of the skin of the evaluation target at once, and also recognize the change in evaluation value from the previous time.

Figure 23:
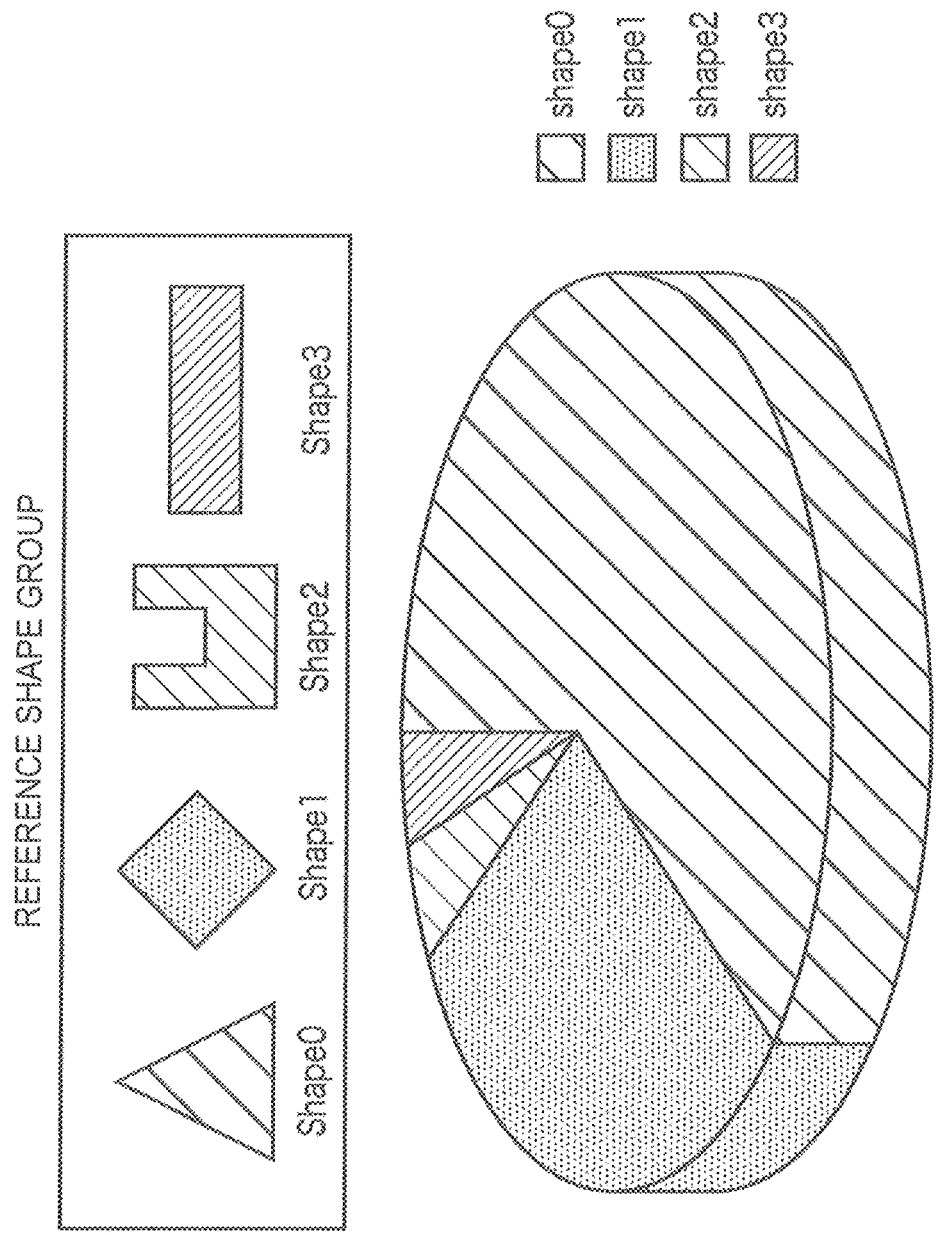
FIG. 23 is a diagram illustrating an example of a screen presenting evaluation results of the texture state of the skin.

In addition, as shown in FIG. 23, the circular graph indicating the distribution of shapes of the skin ridges based on the epidermis shape distribution information $ShapeRatio_i$ may also be presented.

Thereafter, the texture evaluation process is finished.

As described above, the acquired property and the inherent property of the texture state of the skin may be separately evaluated. In addition, it is possible to evaluate the texture state of the skin in further detail based on both of the acquired property and the inherent property. As a result, it is possible to more correctly evaluate the texture state of the skin.

3. Third Embodiment

Next, the third embodiment of the present technology will be described with reference to FIGS. 24 to 29. In the third embodiment, not only the epidermis state but also the dermis state is analyzed to evaluate the texture state of the skin.

[Configuration Example of Image Processing System 301]

Figure 24:
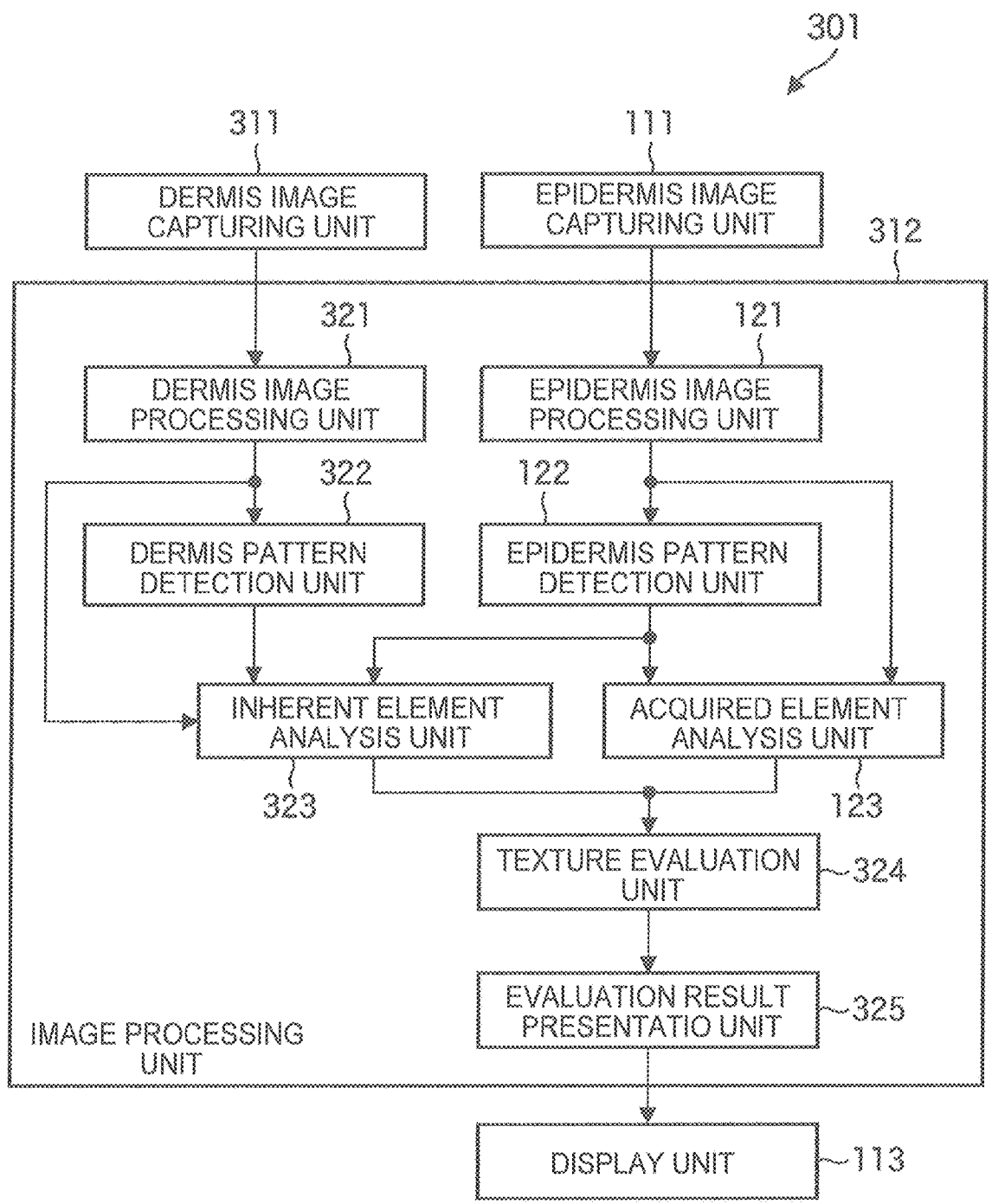
FIG. 24 is a block diagram illustrating an image processing system in accordance with a third embodiment of the present technology.

FIG. 24 is a block diagram illustrating a configuration example of the image processing system 301 in accordance with the third embodiment of the present technology. In addition, like parts corresponding to those in FIG. 16 are designated by like numerals. With respect to parts to be processed in the same manner, the repeated description thereof is properly omitted.

The image processing system 301, as will be described later, detects not only the epidermis patterns but also dermis patterns to perform the skin evaluation.

The image processing system 301 differs from the image processing system 201 of FIG. 16 in that the dermis image capturing unit 311 is additionally disposed and the image processing unit 312 is disposed instead of the image processing unit 211. In addition, the image processing unit 312 differs from the image processing unit 211 in that the dermis image processing unit 321 and the dermis pattern detection unit 322 are additionally disposed, and the inherent element analysis unit 323, the texture evaluation unit 324 and the evaluation result presentation unit 325 are disposed instead of the inherent element analysis unit 221, the texture evaluation unit 222 and the evaluation result presentation unit 223.

The dermis image capturing unit 311, as will be described later, captures the dermis of the skin of the evaluation target, and supplies the captured dermis image to the dermis image processing unit 321 of the image processing unit 312.

The dermis image processing unit 321 has the same configuration as the epidermis image processing unit 121 shown in FIG. 2. Accordingly, the dermis image processing unit 321 performs image correction, single channel extraction, and noise removal on the dermis image. The dermis image processing unit 321 then supplies the noise-removed dermis image to the dermis pattern detection unit 322 and the inherent element analysis unit 323.

The dermis pattern detection unit 322 has the same configuration as the epidermis pattern detection unit 122 shown in FIG. 2. Accordingly, the dermis pattern detection unit 322 performs binarization and labeling process on the noise-removed dermis image to detect patterns of the dermis within the dermis image (hereinafter referred to as dermis patterns).

Here, an example of the dermis patterns detected by the dermis pattern detection unit 322 will be described with reference to FIG. 25.

Figure 25:
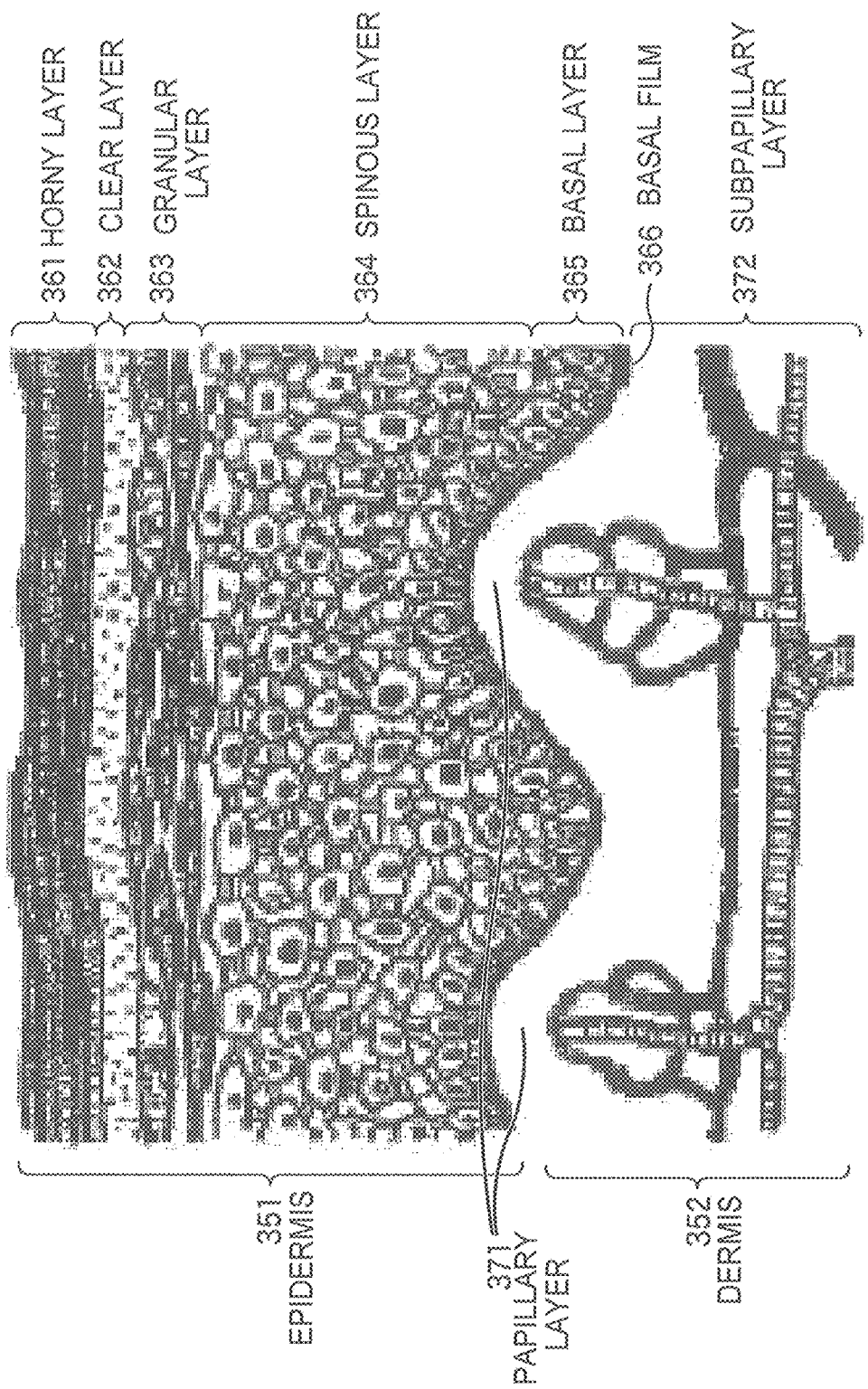
FIG. 25 is a cross-sectional diagram schematically illustrating skin tissues of the skin of a human.

FIG. 25 is a cross-sectional diagram schematically illustrating skin tissues of the skin of a human.

The skin tissues roughly consist of the epidermis 351 and the dermis 352. The epidermis 351 consists of a horny layer 361, a clear layer 362, a granular layer 363, a spinous layer 364, a basal layer 365, and a basal film 366. Meanwhile, the dermis 352 consists of a papillary layer 371, a subpapillary layer 372, and a reticular layer (not shown).

The epidermis 351 and the dermis 352 have different constitutional tissues from each other, and the tissues such as collagen or elastic fiber, which are not present in the epidermis 351, are present in the dermis 352. Accordingly, optical characteristics in the epidermis 351 and the dermis 352 are different from each other. For example, the epidermis 351 has a high optical transparency with respect to red light of visible lights or light in an optical band having a longer wavelength than the near-infrared light whereas the dermis 352 has a low optical transparency with respect to light in the same wavelength range.

The dermis image capturing unit 311, as will be described later, uses the difference in optical characteristics of the epidermis 351 and the dermis 352 to capture the dermis 352. The dermis pattern detection unit 322 detects, as the dermis patterns, regions of elevated patterns having irregular shapes configured mainly by the papillary layer 371 in contact with the epidermis tissue by means of the basal film 366 (hereinafter referred to as papillary layer regions).

In addition, the dermis pattern detection unit 322 counts the number of papillary layer regions within the dermis image (hereinafter referred to as the number of dermis patterns). The dermis pattern detection unit 322 then supplies the dermis pattern detection result indicating the detection result of the number of dermis patterns and the papillary layer regions to the inherent element analysis unit 323.

The inherent element analysis unit 323, as will be described later, performs the inherent element analysis among elements indicating the texture state of the skin based on the epidermis pattern detection result and the dermis pattern detection result. The inherent element analysis unit 323 supplies the analysis result to the texture evaluation unit 324.

The texture evaluation unit 324 evaluates the texture state of the skin of the evaluation target based on the analysis result from the acquired element analysis unit 123 and the analysis result from the inherent element analysis unit 323, and supplies the evaluation result to the evaluation result presentation unit 325.

The evaluation result presentation unit 325 causes the display unit 113 to display the evaluation result of the texture state of the skin of the evaluation target.

[Configuration Example of Dermis Image Capturing Unit 311]

Figure 26:
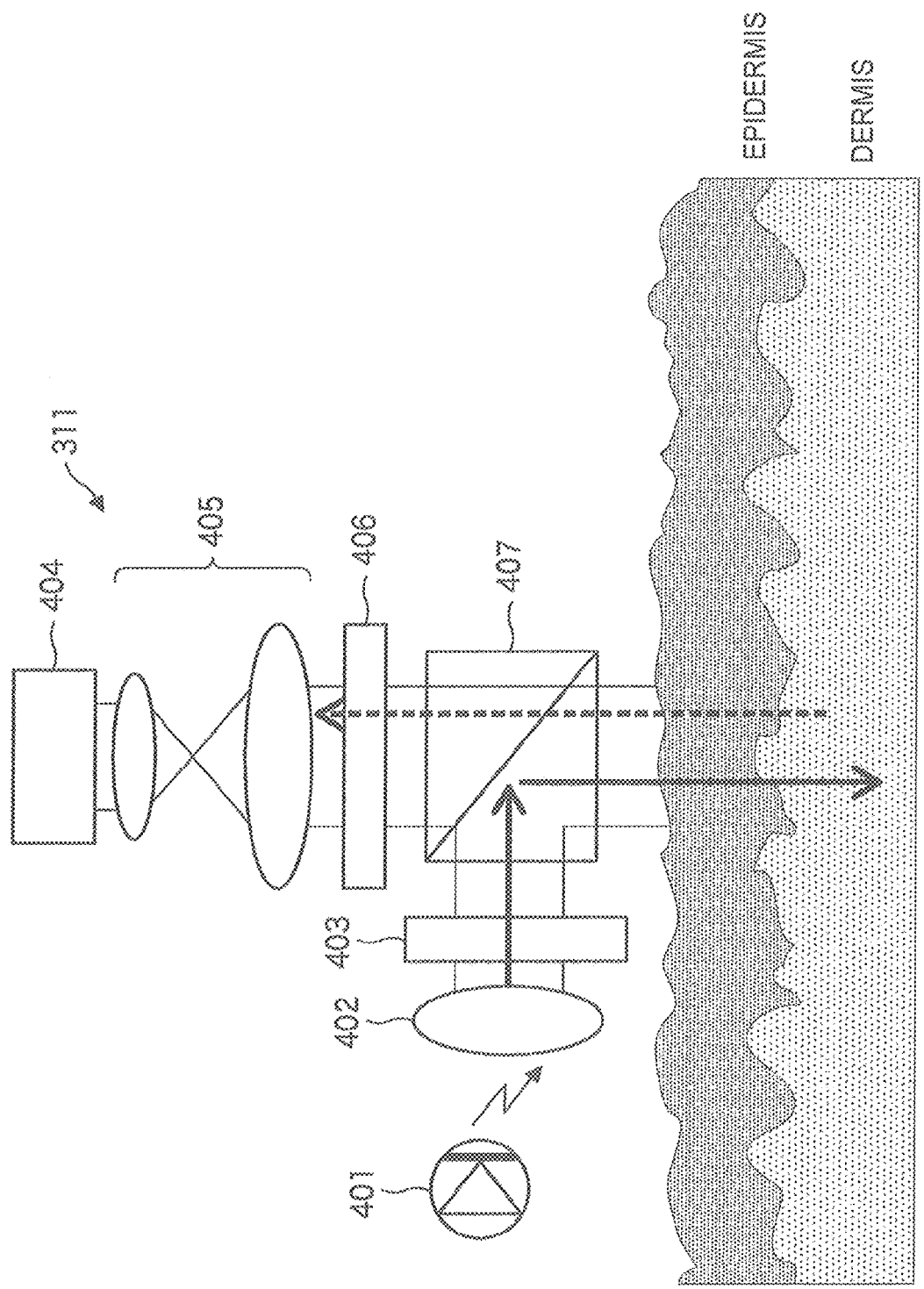
FIG. 26 is a diagram illustrating a configuration example of a dermis image capturing unit.

FIG. 26 illustrates the configuration example of the dermis image capturing unit 311.

The dermis image capturing unit 311 has, as an irradiation optical system, a light source 401, an optical lens 402, and an irradiation portion polarization plate 403. For example, any light source such as an LED may be used as the light source 401. However, it is preferable that a light source emitting long wavelength light such as near-infrared light that transmits the epidermis and is scattered in the dermis be used as the light source 401. Accordingly, it is possible to obtain tissue patterns using optical characteristics such as scattering or birefringence in the tissues below the epidermis.

In addition, the dermis image capturing unit 311 has, as an imaging optical system, a capturing element that receives light 404 (for example, a CCD image sensor, a CMOS image sensor, and so forth), an imaging lens group 405, and a light receiving portion polarization plate 406. In addition, a half-mirror 407 is disposed on an optical path between the irradiation optical system and the imaging optical system, and is orthogonal with respect to the irradiation optical system and the imaging optical system.

In the dermis image capturing unit 311, the irradiation light from the light source 401 is irradiated on the skin while the vibration direction is limited to one direction by the irradiation portion polarization plate 403. In addition, although the light receiving portion polarization plate 406 is disposed in the imaging optical system, this light receiving portion polarization plate is configured such that the vibration direction is orthogonal to the irradiation portion polarization plate 403. Accordingly, the simple reflected light in the epidermis tissue is shielded by the light receiving portion polarization plate 406 because the vibration direction is caused to be orthogonal to the light receiving portion polarization plate 406.

Irradiation lights irradiated on the skin from the irradiation optical system reach as far as deep skin tissues (for example, the dermis tissue), and the polarization is resolved by scattering or birefringence occurring due to various tissues. These lights transmit the half-mirror 407 as back-scattered lights to be guided to the imaging optical system. However, the polarization is resolved as described above, so that the lights transmit the light receiving portion polarization plate 406 to reach as far as the capturing element 404.

Accordingly, it is possible to capture the patterns having the irregular shapes of the dermis by separating the reflected and scattered lights in the epidermis tissues from the lights having different phases that have passed through the birefringence tissues (dermis tissues).

The capturing element 404 supplies the obtained dermis image to the dermis image processing unit 321.

[Configuration Example of Inherent Element Analysis Unit 323]

Figure 27:
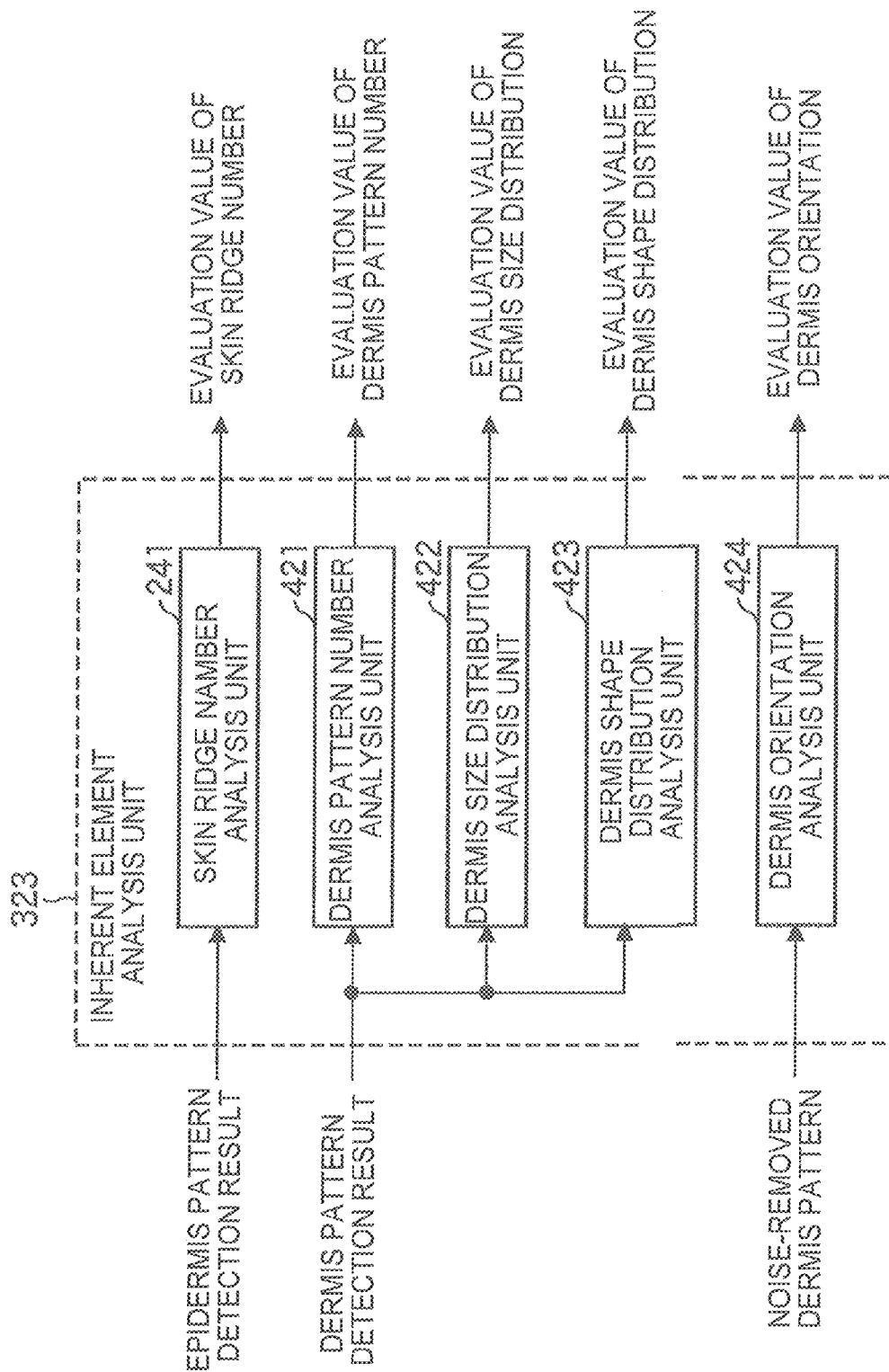
FIG. 27 is a block diagram illustrating a configuration example of an inherent element analysis unit.

FIG. 27 is a block diagram illustrating the configuration example of the inherent element analysis unit 323. In addition, like parts corresponding to those in FIG. 17 are designated by like numerals, and with respect to parts to be processed in the same manner, the repeated description thereof is properly omitted.

The inherent element analysis unit 323 differs from the inherent element analysis unit 221 of FIG. 17 in that the dermis pattern number analysis unit 421, the dermis size distribution analysis unit 422, the dermis shape distribution analysis unit 423, and the dermis orientation analysis unit 424 are additionally disposed.

The dermis pattern number analysis unit 421 performs the same process as the skin ridge number analysis unit 241 based on the dermis pattern detection result. That is, the dermis pattern number analysis unit 421 calculates the evaluation value of the number of dermis patterns that is the index for indicating the fineness of the skin texture based on the number of dermis patterns included in the dermis pattern detection result. The dermis pattern number analysis unit 421 supplies the calculated evaluation value of the number of dermis patterns to the texture evaluation unit 324.

The dermis size distribution analysis unit 422 analyzes the distribution of sizes of the dermis patterns by performing the same process as the epidermis size distribution analysis unit 171 of the acquired element analysis unit 123 of FIG. 3 based on the dermis pattern detection result. In particular, the dermis size distribution analysis unit 422 analyzes the distribution of sizes of the papillary layer regions, and calculates the evaluation value of the dermis size distribution indicating the uniformity of sizes of the papillary layer regions. The dermis size distribution analysis unit 422 supplies the calculated evaluation value of the dermis size distribution to the texture evaluation unit 324.

The dermis shape distribution analysis unit 423 analyzes the distribution of shapes of the dermis patterns by performing the same process as the epidermis shape distribution analysis unit 172 of the acquired element analysis unit 123 of FIG. 3 based on the dermis pattern detection result. In particular, the dermis shape distribution analysis unit 423 analyzes the distribution of shapes of the papillary layer regions, and calculates the evaluation value of the dermis shape distribution indicating the uniformity of shapes of the papillary layer regions. The dermis shape distribution analysis unit 423 supplies the calculated evaluation value of the dermis shape distribution to the texture evaluation unit 324.

The dermis orientation analysis unit 424 analyzes the orientation of the dermis patterns by performing the same process as the epidermis orientation analysis unit 174 of the acquired element analysis unit 123 of FIG. 3 based on the noise-removed dermis image. In particular, the dermis orientation analysis unit 424 analyzes the distribution of edge directions of the papillary layer regions, and calculates the evaluation value of the dermis orientation indicating the uniformity of distribution of edge directions of the papillary layer regions. The dermis orientation analysis unit 424 supplies the calculated evaluation value of the dermis orientation to the texture evaluation unit 124.

In addition, it is known that the dermis patterns formed by the papillary layers or the like have many inherent elements and the change in dermis patterns due to aging, health, skin care and so forth is small. Accordingly, the evaluation value of the number of dermis patterns, the evaluation value of the dermis size distribution, the evaluation value of the dermis shape distribution, and the evaluation value of the dermis orientation become indexes for evaluating inherent properties of the texture state of the skin.

[Texture Evaluation Process]

Figure 28:
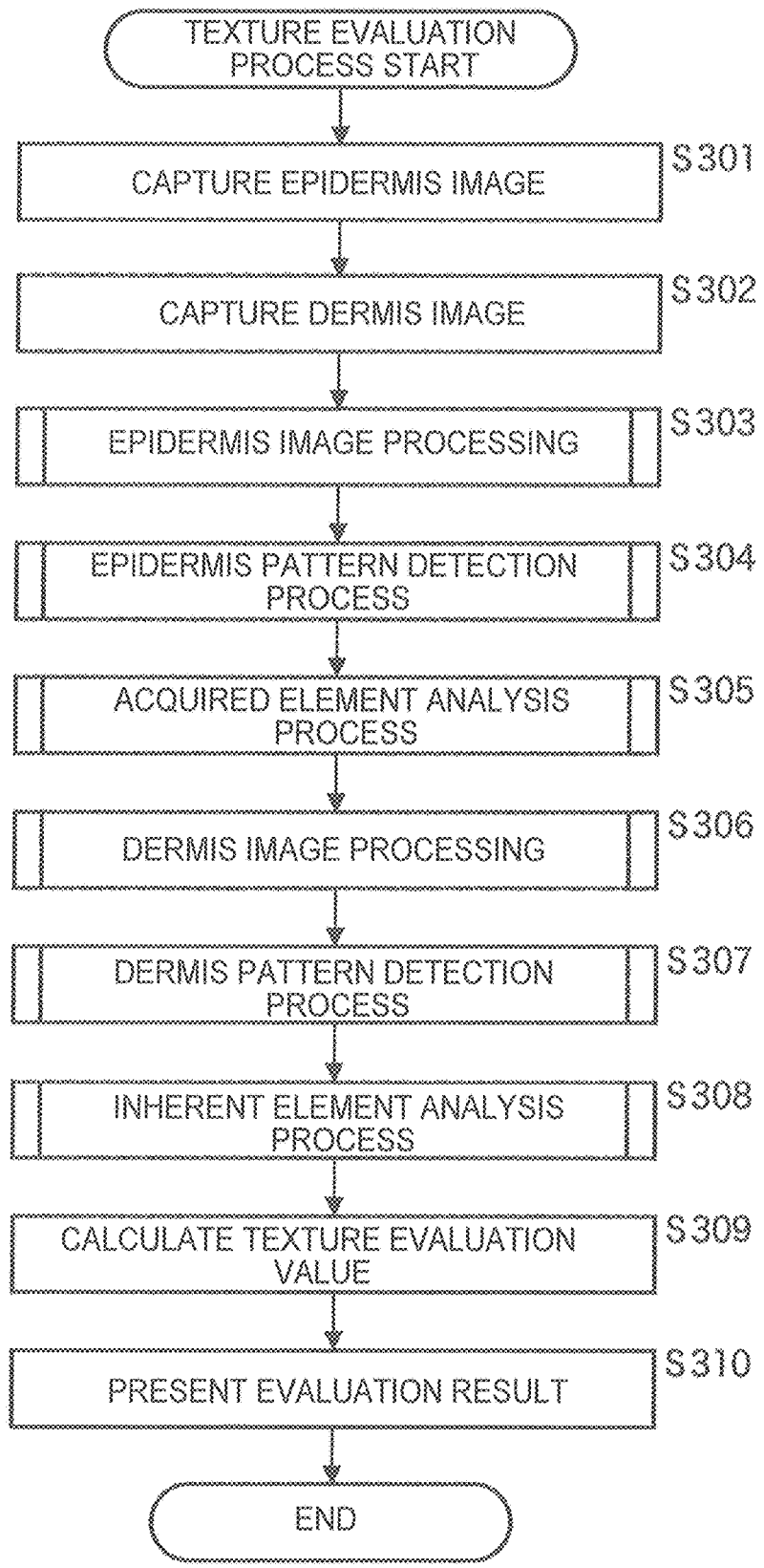
FIG. 28 is a flow chart illustrating a texture evaluation process.

Next, the texture evaluation process carried out by the image processing system 301 will be described with reference to the flow chart of FIG. 28.

In addition, for example, this process is initiated when the instruction to carry out the texture evaluation process is input through an input unit not shown in the image processing system 301.

In step S301, the epidermis image is captured in the same manner as in step S1 of FIG. 5.

In step S302, the dermis image capturing unit 311 captures the dermis image. That is, the dermis image capturing unit 311, as described above with reference to FIG. 26, captures the dermis of the skin of the evaluation target, and supplies the captured dermis image to the dermis image processing unit 321.

In addition, it is preferable that the capturing interval between the epidermis image and the dermis image be set to as short a time as possible and capturing ranges of the epidermis image and the dermis image be set to be almost equal to each other. In addition, the order of capturing the epidermis image and the dermis image may be reversed.

In steps S303 to S305, the same process as in steps S2 to S4 of FIG. 5 is performed. Through this process, the evaluation value of the epidermis size distribution $Eeval_{size}$, the evaluation value of the epidermis shape distribution $Eeval_{shape}$, the epidermis shape distribution information $ShapeRatio_i$, the evaluation value of the epidermis orientation $Eeval_{direction}$, and the number of skin ridges $N_{ridge}$ are obtained, and are then supplied to the texture evaluation unit 324.

In step S306, the dermis image processing unit 321 performs the dermis image processing. That is, the dermis image processing unit 321 performs, on the dermis image, the same process as that performed on the epidermis image by the epidermis image processing unit 121 in step S2 of FIG. 5 described above. The dermis image processing unit 321 then supplies the noise-removed dermis image to the dermis pattern detection unit 322 and the inherent element analysis unit 323.

In step S307, the dermis pattern detection unit 322 performs the dermis pattern detection process. That is, the dermis pattern detection unit 322 performs, on the noise-removed dermis pattern, the same process as that performed on the noise-removed epidermis image by the epidermis pattern detection unit 122 in step S3 of FIG. 5 described above.

Accordingly, the dermis pattern detection unit 322 detects a plurality of papillary layer regions from the noise-removed dermis image. In addition, the dermis pattern detection unit 322 counts the number of dermis patterns $N_{dermis}$ that is the number of papillary layer regions within the dermis image. The dermis pattern detection unit 322 supplies the dermis pattern detection result indicating the detection result of the number of dermis patterns and the papillary layer regions to the inherent element analysis unit 323.

In step S308, the inherent element analysis unit 323 performs the inherent element analysis process.

[Inherent Element Analysis Process]

Figure 29:
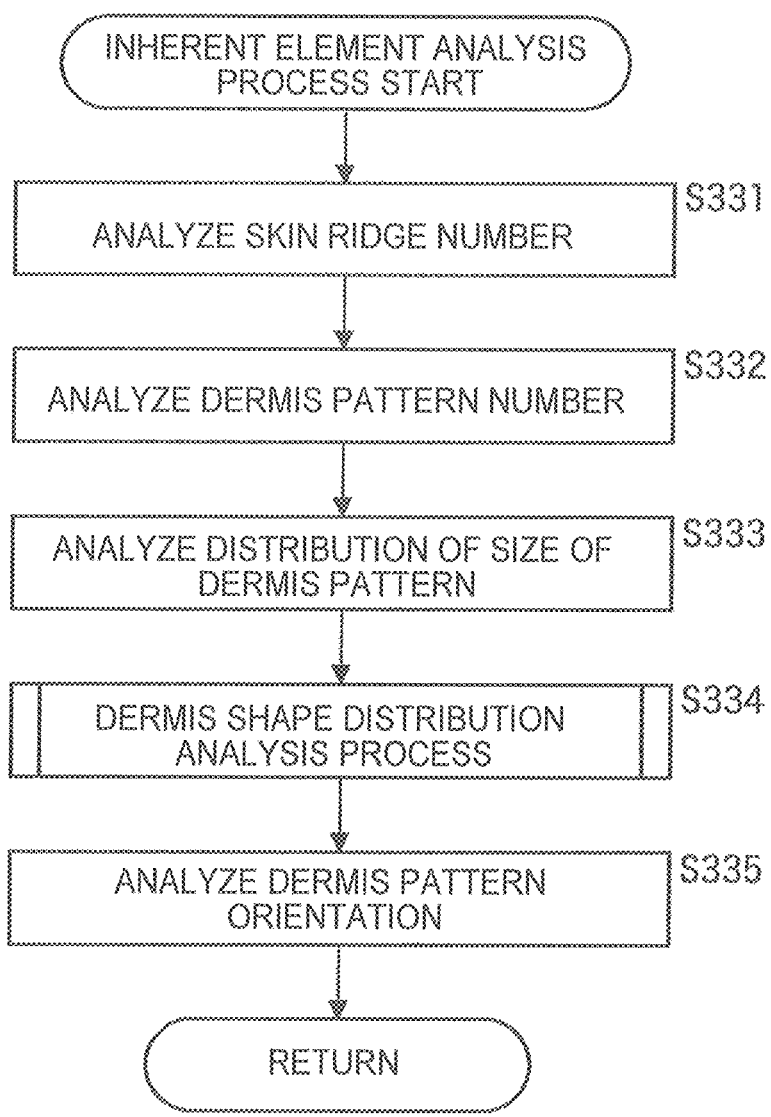
FIG. 29 is a flow chart illustrating an inherent element analysis process.

Here, details of the inherent element analysis process will be described with reference to the flow chart of FIG. 29.

Figure 19:
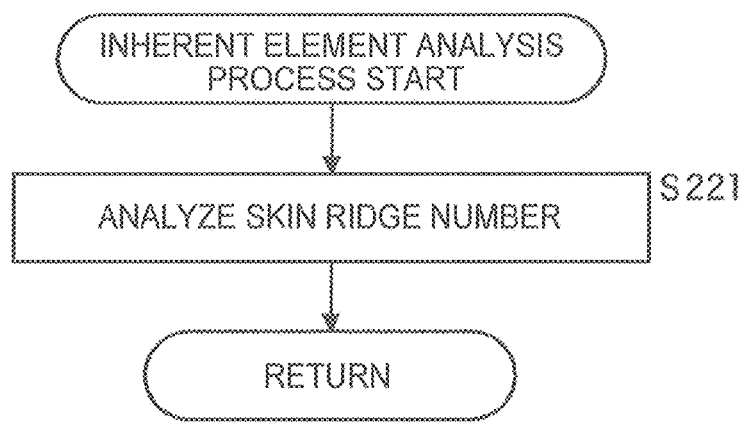
FIG. 19 is a flow chart illustrating an inherent element analysis process.

In step S331, the number of skin ridges is analyzed in the same manner as in the process of step S221 of FIG. 19 described above. The skin ridge number analysis unit 241 supplies the evaluation value of the number of skin ridges $Eeval_{num}$ to the texture evaluation unit 324.

In step S332, the dermis pattern number analysis unit 421 analyzes the number of dermis patterns. In particular, the dermis pattern number analysis unit 421 calculates the evaluation value of the number of dermis patterns $Deval_{num}$ using the number of dermis patterns $N_{dermis}$ by performing the same process as the case of calculating the evaluation value of the number of skin ridges $Eeval_{num}$ by the skin ridge number analysis unit 241 in step S221 of FIG. 19.

Accordingly, the evaluation value of the number of dermis patterns $Deval_{num}$ increases when the number of dermis patterns $N_{dermis}$ increases in the same manner as the evaluation value of the number of skin ridges $Eeval_{num}$. In addition, since the number of dermis patterns $N_{dermis}$ indicates the number of dermis patterns within the dermis image (i.e., the number of dermis patterns per unit area), it may be said that the skin texture is finer when the number of dermis patterns $N_{dermis}$ increases. Accordingly, the evaluation value of the number of dermis patterns $Deval_{num}$ becomes the index for indicating the fineness of the skin texture.

The dermis pattern number analysis unit 421 supplies the evaluation value of the number of dermis patterns $Deval_{num}$ to the texture evaluation unit 324.

In step S333, the dermis size distribution analysis unit 422 analyzes the distribution of sizes of the dermis patterns. In particular, the dermis size distribution analysis unit 422 calculates the evaluation value of the dermis size distribution $Deval_{size}$ based on the detection result of the papillary layer regions by performing the same process as the case of calculating the evaluation value of the epidermis size distribution $Eeval_{size}$ by the epidermis size distribution analysis unit 171 in step S61 of FIG. 9.

Accordingly, the evaluation value of the dermis size distribution $Deval_{size}$ increases when the variance in sizes of the papillary layer regions is smaller in the same manner as the evaluation value of the epidermis size distribution $Eeval_{size}$. That is, the evaluation value of the dermis size distribution $Deval_{size}$ increases when the variations in size of the papillary layer regions are smaller. Accordingly, the evaluation value of the dermis size distribution $Deval_{size}$ becomes the index for indicating the uniformity of sizes of the papillary layer regions.

The dermis size distribution analysis unit 422 supplies the evaluation value of the dermis size distribution $Deval_{size}$ to texture evaluation unit 324.

In step S334, the dermis shape distribution analysis unit 423 performs the dermis shape distribution analysis process. In particular, the dermis shape distribution analysis unit 423 calculates the evaluation value of the dermis shape distribution $Deval_{shape}$ based on the detection result of the papillary layer regions by performing the same process as the case of calculating the evaluation value of the epidermis shape distribution $Eeval_{shape}$ by the epidermis shape distribution analysis unit 172 in the epidermis shape distribution analysis process 1 of FIG. 12.

Accordingly, the evaluation value of the dermis shape distribution $Deval_{shape}$ increases when the variations in shape of the papillary layer regions are smaller in the same manner as the evaluation value of the epidermis shape distribution $Eeval_{shape}$. Accordingly, the evaluation value of the dermis shape distribution $Deval_{shape}$ is the index for indicating the uniformity of shapes of the papillary layer regions.

The dermis shape distribution analysis unit 423 supplies the evaluation value of the dermis shape distribution $Deval_{shape}$ to the texture evaluation unit 324.

In step S335, the dermis orientation analysis unit 424 analyzes the orientation of dermis patterns. In particular, the dermis orientation analysis unit 424 calculates the evaluation value of the dermis orientation $Deval_{direction}$ based on the noise-removed dermis image by performing the same process as the case of calculating the evaluation value of the epidermis orientation $Eeval_{direction}$ by the epidermis orientation analysis unit 174 in step S64 of FIG. 9.

Accordingly, the evaluation value of the dermis orientation $Deval_{direction}$ increases when the edge directions of the papillary layer regions are uniformly distributed in four directions such as vertical, horizontal and sloped directions (0°, 45°, 90°, and 135°) in the same manner as the evaluation value of the epidermis orientation $Eeval_{direction}$. Accordingly, the evaluation value of the dermis orientation $Deval_{direction}$ is the index for indicating the uniformity of the distribution of edge directions of the papillary layer regions.

The dermis orientation analysis unit 424 supplies the evaluation value of the dermis orientation $Deval_{direction}$ to the texture evaluation unit 324.

Referring back to FIG. 28, in step S309, the texture evaluation unit 324 calculates the texture evaluation value.

For example, the texture evaluation unit 324 calculates the texture evaluation value $eval4_{total}$ by means of Equation (23) below.

$$eval4_{total} = \alpha_{inherent} \times Eeval_{num} \times Deval_{num} \times Deval_{size} \times Deval_{shape} \times Deval_{direction} + (1 - \alpha_{inherent}) \times eval1_{total} \quad (23)$$

In addition, $\alpha_{inherent}$ and $eval1_{total}$ are same as those of Equation (22) described above.

The texture evaluation value $eval4_{total}$ is the value compared with the texture evaluation value $eval3_{total}$ of Equation (22) to evaluate not only the epidermis state but also the dermis state. Accordingly, the texture evaluation value $eval4_{total}$ is the index that is compared with the texture evaluation value $eval3_{total}$ to evaluate the texture state of the skin in further detail.

In addition, in Equation (23), the texture evaluation value $eval2_{total}$ of Equation (20) may be used instead of the texture evaluation value $eval1_{total}$.

The texture evaluation unit 324 supplies the evaluation result of the texture state of the skin to the evaluation result presentation unit 223. Here, the texture evaluation unit 324 supplies not only the texture evaluation value $eval4_{total}$ but also each evaluation value used for calculating the texture evaluation value $eval4_{total}$ to the evaluation result presentation unit 325.

Figure 18:
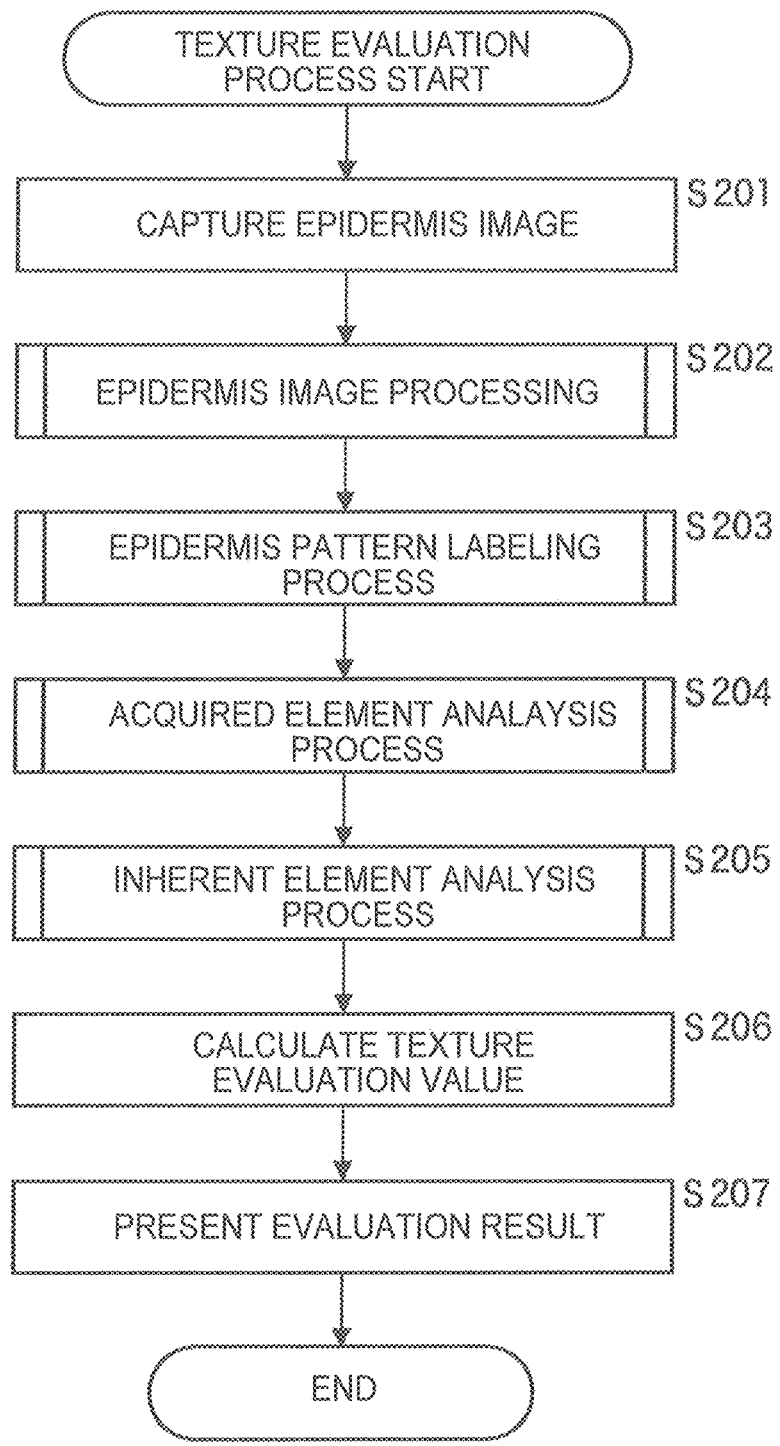
FIG. 18 is a flow chart illustrating a texture evaluation process.

In step S307, the evaluation result is presented in the same manner as the process of step S207 of FIG. 18.

Thereafter, the texture evaluation process is finished.

As described above, it is possible to evaluate the texture state of the skin in further detail based on the dermis state in addition to the epidermis state. As a result, it is possible to more correctly evaluate the texture state.

4. Modification

Hereinafter, modification examples of the embodiments of the present technology will be described.

Modification Example 1

The method of calculating the degree of difference (or the degree of similarity) in shape between the skin ridge regions or the papillary layer regions is not limited to the methods described above with reference to FIG. 12, but may employ any methods. For example, as described below, Dynamic Programming (DP) matching may be employed to calculate the degree of similarity of shapes.

First, contour extraction, thinning, and vectorization are performed on the region A to obtain the vector characteristic amount A indicated in Equations (24) and (25).

$$A = \{a_1, a_2, \ldots, a_m\} \quad (24)$$

$$a_i = (x_{is}, y_{is}, x_{ie}, y_{ie}) \quad (25)$$

In addition, $x_{is}$ and $y_{is}$ are coordinates of the start points of the vector $a_i$, and $x_{ie}$ and $y_{ie}$ are coordinates of the end points of the vector $a_i$.

In addition, the same process is also performed on the region B for comparison with the region A to obtain the vector characteristic amount B indicated in Equations (26) and (27).

$$B = \{b_1, b_2, \ldots, b_m\} \quad (26)$$

$$b_j = (x_{js}, y_{js}, x_{je}, y_{je}) \quad (27)$$

In addition, $x_{js}$ and $y_{js}$ are coordinates of the start points of the vector $b_j$, and $x_{je}$ and $y_{je}$ are coordinates of the end points of the vector Next, the degree of similarity $h(a_i, b_j)$ between one component vector $a_i$ of the region A and one component vector $b_j$ of the region B is calculated as in Equations (28) and (29) below.

$$h(a_i, b_j) = \min \begin{cases} h(a_{i-1}, b_{j-1}) + 2d(a_i, b_j) \\ h(a_{i-1}, b_j) + d(a_i, b_j) \\ h(a_i, b_{j-1}) + d(a_i, b_j) \end{cases} \quad (28)$$

$$d(a_i, b_j) = \|a_i - b_j\| \quad (29)$$

For example, the degree of similarity S(A,B) between the region A and the region B is calculated, for example, as in Equation (30) below.

$$S(A, B) = \sum_{ij} h(a_i, b_j) \quad (30)$$

For example, it is possible to use this degree of similarity S(A,B) instead of the degree of difference D(A,B) calculated in Equations (9a) to (9c) described above.

Modification Example 2

Figure 14:
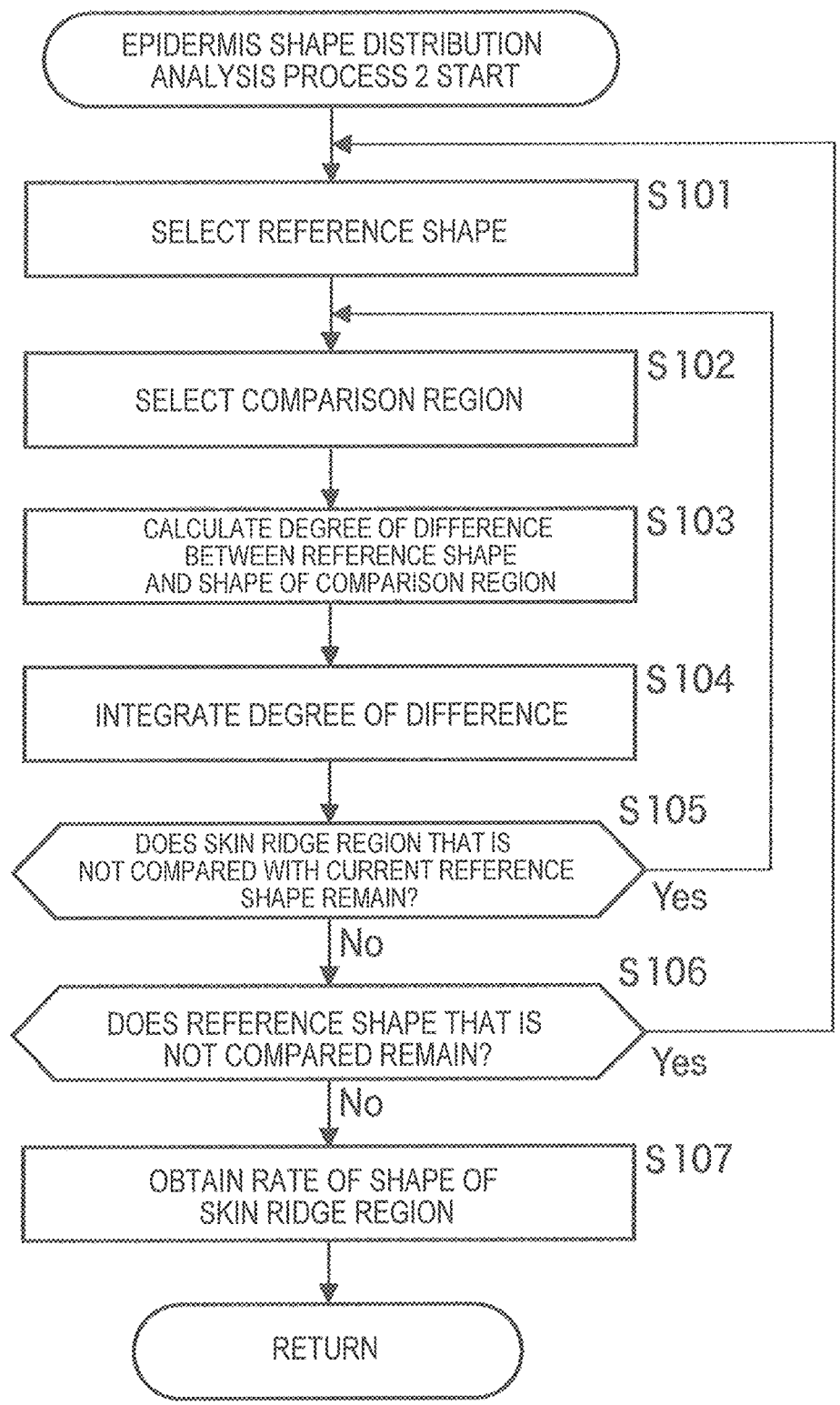
FIG. 14 is a flow chart illustrating epidermis shape distribution analysis process 2.

The process of classifying the shapes of the skin ridge regions in the epidermis shape distribution analysis process 2 of FIG. 14 is not limited to the method described above. For example, Support Vector Machine (SVM) and so forth may be employed to perform the learning-based shape classification using reference shapes. Alternatively, for example, clustering schemes such as K-means method without using the reference shape may be employed to perform the shape classification.

Modification Example 3

The process of analyzing edge directions of the skin ridge regions or papillary layer regions is not limited to the method described above method. For example, a fast Fourier transformation (FFT) may be performed on the noise-removed dermis image or the noise-removed epidermis image to obtain the histogram with respect to each angle from the spectral image of the noise-removed dermis image or the noise-removed epidermis image, and the distribution of the edge directions of the skin ridge regions or the papillary layer regions may be analyzed based on the shapes of the histogram.

Modification Example 4

The configuration of the dermis image capturing unit 311 of FIG. 26 is merely an example, and other configurations may be employed for the same. For example, the dermis image may be captured by the capturing device using a micro lens array (MLA) employed for biometric authentication such as fingerprint authentication.

Modification Example 5

The method of presenting the evaluation result described with reference to FIGS. 21 to 23 is merely an example, and other methods may be employed to present the evaluation result. In addition, besides the image, voices or the like may be used to present the evaluation result.

Modification Example 6

It is not necessary that the texture evaluation values $eval1_{total}$ to $eval4_{total}$ be calculated by all evaluation values indicated in each equation, but evaluation values to be used may be selected in accordance with purpose or use. For example, in Equation (19), one or two among the evaluation value of the epidermis size distribution $Eeval_{size}$, the evaluation value of the epidermis shape distribution $Eeval_{shape}$, and the evaluation value of the epidermis orientation $Eeval_{direction}$ may be used to calculate the texture evaluation value $eval1_{total}$.

In addition, for example, it is possible to remove constitutional elements of the acquired element analysis unit 123 of FIG. 3 or the inherent element analysis unit 323 of FIG. 27 in accordance with the selection of the evaluation value used for calculating the texture evaluation value.

Modification Example 7

Figure 13:
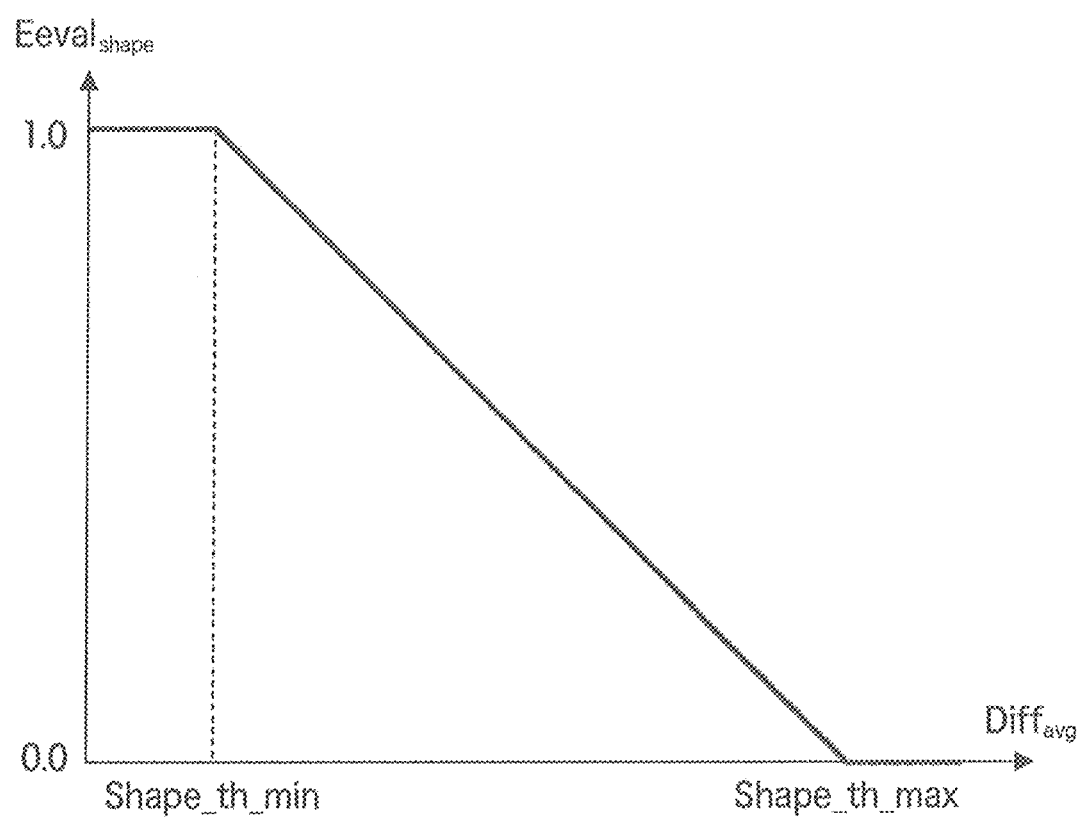
FIG. 13 is a diagram illustrating an example of a normalization curve for calculating evaluation values of epidermis shape distribution.
Figure 20:
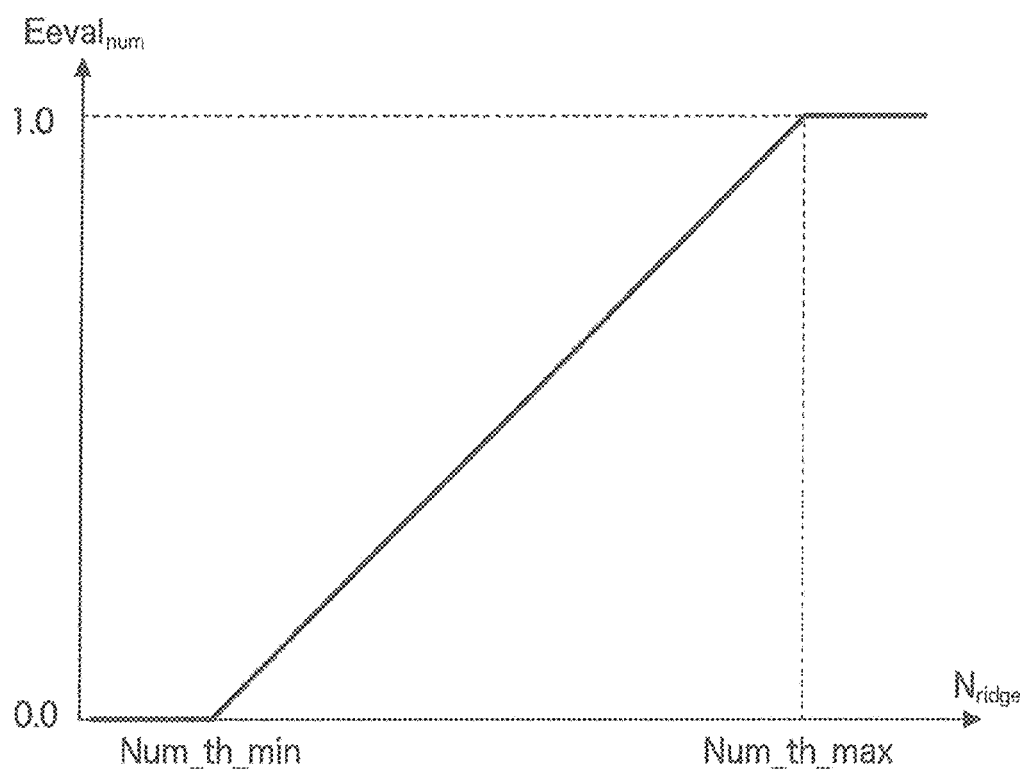
FIG. 20 is a diagram illustrating an example of a normalization curve for calculating evaluation values of the number of skin ridges.

The shapes of the normalization curves in FIGS. 11, 13, and 20 are merely examples, and it is possible to use a curve that has a different shape and indicates the same monotonic increase or monotonic decrease as each of the normalization curves of FIGS. 11, 13, and 20.

In addition, for example, it is possible to apply the present technology to the system or device that evaluates and diagnoses the skin state as the beauty or health index. In addition, it is possible to apply the present technology to the case in which the skin state of a living body other than a human is evaluated and diagnosed.

Configuration Example of Computer

The processes described above can be executed by any of hardware or software. When a series of processes is executed by software, a program constituting the software is installed in a computer. Here, the computer includes a computer built in dedicated hardware or, for example, a general-purpose personal computer capable of executing various functions by installing various programs.

Figure 30:
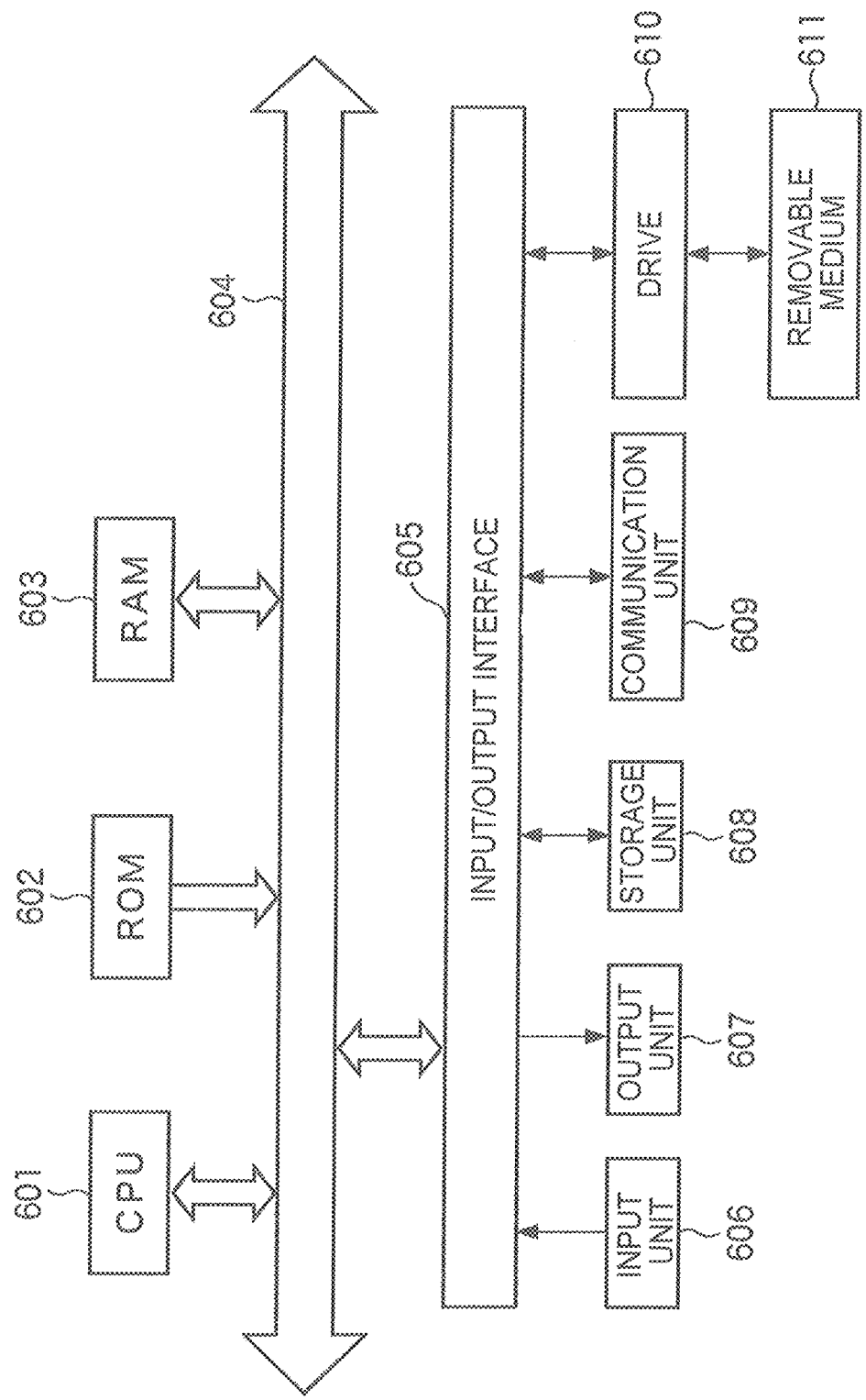
FIG. 30 is a block diagram illustrating a configuration example of a computer.

FIG. 30 is a block diagram showing an example of the hardware configuration of a computer which executes the series of processes using a program.

In the computer, a CPU (Central Processing Unit) 601, a ROM (Read Only Memory) 602, and a RAM (Random Access Memory) 603 are connected to each other via a bus 604.

To the bus 604, an input/output interface 605 is also connected. Connected to the input/output interface 605 are an input unit 606, an output unit 607, a storage unit 608, a communication unit 609, and a drive 610.

The input unit 607 includes a keyboard, a mouse, a microphone, and the like. The output unit 608 includes a display, a speaker, and the like. The storage unit 609 includes a hard disk, a non-volatile memory, and the like. The communication unit 610 includes a network interface and the like. The drive 910 drives a removable medium 611 such as a magnetic disk, an optical disc, a magneto-optical disk, or a semiconductor memory.

In the thus configured computer, for example, the CPU 601 executes a program stored in the storage unit 608 by loading the program in the RAM 603 via the input/output interface 605 and the bus 604, and thereby performing the above-mentioned series of processes.

The program executed by the computer (CPU 601) is provided by being recorded in the removable medium 611 serving as a package medium, for example. Further, the program can be provided via a wired or wireless transmission medium such as a local area network, the Internet, and digital satellite broadcasting.

In the computer, the program can be installed in the storage unit 608 via the input/output interface 605, by mounting the removable medium 611 on the drive 610. Further, the program can be received by the communication unit 609 via the wired or wireless transmission medium and can be installed in the storage unit 608. In addition, the program can be installed in the ROM 602 and the storage unit 608 in advance.

It should be noted that the program executed by a computer may be a program that is processed in time series according to the sequence described in this specification or a program that is processed in parallel or at necessary timing such as upon calling.

In addition, the term system means a general device composed of a plurality of devices, means, and so forth in the present technology.

It should be understood by those skilled in the art that various modifications, combinations, sub-combinations and alterations may occur depending on design requirements and other factors insofar as they are within the scope of the appended claims or the equivalents thereof.

Additionally, for example, the present technology may also be configured as below.

(1) An image processing device, including:
an epidermis pattern detection unit configured to detect epidermis patterns that are patterns of an epidermis in an epidermis image captured from the epidermis of skin;
an analysis unit configured to analyze uniformity of shapes of the epidermis patterns; and
an evaluation unit configured to evaluate a texture state of the skin based on the uniformity of shapes of the epidermis patterns.

(2) The image processing device according to (1), wherein the analysis unit further analyzes at least one of uniformity of sizes of the epidermis patterns and uniformity of distributions of edge directions of the epidermis patterns, and the evaluation unit further evaluates the texture state of the skin based on at least one of the uniformity of sizes of the epidermis patterns and the uniformity of distribution of edge directions of the epidermis patterns.

(3) The image processing device according to (1) or (2), wherein the analysis unit further analyzes a ratio at which the epidermis patterns have predetermined shapes, and the evaluation unit further evaluates the texture state of the skin based on the ratio at which the epidermis patterns have the predetermined shapes.

(4) The image processing device according to any one of (1) to (3), wherein the epidermis patterns are patterns formed on the epidermis by skin ridges or skin grooves.

(5) An image processing method performed by an image processing device configured to evaluate a texture state of skin, including:
detecting epidermis patterns that are patterns of an epidermis in an epidermis image captured from the epidermis of the skin;
analyzing uniformity of shapes of the epidermis patterns; and
evaluating the texture state of the skin based on the uniformity of shapes of the epidermis patterns.

(6) A program for causing a computer to execute operations including:
detecting epidermis patterns that are patterns of an epidermis in an epidermis image captured from the epidermis of skin;
analyzing uniformity of shapes of the epidermis patterns; and
evaluating a texture state of the skin based on the uniformity of shapes of the epidermis patterns.

(7) An image processing device, including:
an epidermis pattern detection unit configured to detect epidermis patterns that are patterns of an epidermis in an epidermis image captured from the epidermis of skin;
an acquired element analysis unit configured to analyze acquired elements among elements indicating a texture state of the skin based on the detected epidermis patterns;
an inherent element analysis unit configured to analyze inherent elements among the elements indicating the texture state of the skin based on the detected epidermis patterns; and
an evaluation unit configured to evaluate the texture state of the skin based on the analysis result from the acquired elements and the analysis result from the inherent elements.

(8) The image processing device according to (7), wherein the acquired element analysis unit analyzes, as the acquired elements, at least one of uniformity of shapes of the epidermis patterns, uniformity of sizes of the epidermis patterns, and uniformity of distribution of edge directions of the epidermis patterns, and the inherent element analysis unit analyzes, as the inherent elements, the number of the epidermis patterns per unit area.

(9) The image processing device according to (7) or (8), wherein the evaluation unit calculates an evaluation value of the texture state of the skin by weighting and adding an evaluation value based on the analysis result from the acquired elements and an evaluation value based on the analysis result from the inherent elements.

(10) The image processing device according to any one of (7) to (9), wherein the epidermis patterns are patterns formed on the epidermis by skin ridges or skin grooves.

(11) An image processing method performed by an image processing device configured to evaluate a texture state of skin, including:
detecting epidermis patterns that are patterns of an epidermis in an epidermis image captured from the epidermis of the skin;
analyzing acquired elements among elements indicating the texture state of the skin based on the detected epidermis patterns;
analyzing inherent elements among the elements indicating the texture state of the skin based on the detected epidermis patterns; and
evaluating the texture state of the skin based on the analysis result from the acquired elements and the analysis result from the inherent elements.

(12) A program for causing a computer to execute operations including:
detecting epidermis patterns that are patterns of an epidermis in an epidermis image captured from the epidermis of skin;

analyzing acquired elements among elements indicating a texture state of the skin based on the detected epidermis patterns;

analyzing inherent elements among the elements indicating the texture state of the skin based on the detected epidermis patterns; and evaluating the texture state of the skin based on the analysis result from the acquired elements and the analysis result from the inherent elements.

(13) An image processing device, including:

an epidermis pattern detection unit configured to detect epidermis patterns that are patterns of an epidermis in an epidermis image captured from the epidermis of skin;

a dermis pattern detection unit configured to detect dermis patterns that are patterns of a dermis in a dermis image captured from the dermis of the skin;

an acquired element analysis unit configured to analyze acquired elements among elements indicating a texture state of the skin based on the detected epidermis patterns;

an inherent element analysis unit configured to analyze inherent elements among the elements indicating the texture state of the skin based on the detected dermis patterns; and an evaluation unit configured to evaluate the texture state of the skin based on the analysis result from the acquired elements and the analysis result from the inherent elements.

(14) The image processing device according to (13), wherein the acquired element analysis unit analyzes, as the acquired elements, at least one of uniformity of shapes of the epidermis patterns, uniformity of sizes of the epidermis patterns, and uniformity of distribution of edge directions of the epidermis patterns, and the inherent element analysis unit analyzes, as the inherent elements, at least one of uniformity of shapes of the dermis patterns, uniformity of sizes of the dermis patterns, uniformity of distribution of edge directions of the dermis patterns, and the number of the dermis patterns per unit area.

(15) The image processing device according to (13) or (14), wherein the inherent element analysis unit further analyzes, as the inherent element, the number of the epidermis patterns per unit area based on the detected epidermis patterns.

(16) The image processing device according to any one of (13) to (15), wherein the evaluation unit calculates an evaluation value of the texture state of the skin by weighting and adding an evaluation value based on the analysis result from the acquired elements and an evaluation value based on the analysis result from the inherent elements.

(17) The image processing device according to any one of (13) to (16), wherein the epidermis patterns are patterns formed on the epidermis by skin ridges or skin grooves, and the dermis patterns are patterns formed on the dermis by papillary layers.

(18) An image processing method performed by an image processing device configured to evaluate a texture state of skin, including:

detecting epidermis patterns that are patterns of an epidermis in an epidermis image captured from the epidermis of the skin;

detecting dermis patterns that are patterns of a dermis in a dermis image captured from the dermis of the skin;

analyzing acquired elements among elements indicating the texture state of the skin based on the detected epidermis patterns;

analyzing inherent elements among the elements indicating the texture state of the skin based on the detected dermis patterns; and evaluating the texture state of the skin based on the analysis result from the acquired elements and the analysis result from the inherent elements.

(19) A program for causing a computer to execute operations including:

detecting epidermis patterns that are patterns of an epidermis in an epidermis image captured from the epidermis of skin;

detecting dermis patterns that are patterns of a dermis in a dermis image captured from the dermis of the skin;

analyzing acquired elements among elements indicating a texture state of the skin based on the detected epidermis patterns;

analyzing inherent elements among the elements indicating the texture state of the skin based on the detected dermis patterns; and evaluating the texture state of the skin based on the analysis result from the acquired elements and the analysis result from the inherent elements.

(20) A computer readable recording medium having recorded thereon a program according to (6), (12), or (19).

What is claimed is:

1. An image processing device, comprising:
   a processing device configured to:
   detect epidermis patterns that are patterns of an epidermis in an epidermis image captured from the epidermis of skin;
   analyze acquired elements among elements indicating a texture state of the skin based on the detected epidermis patterns, wherein the acquired elements analyzed include uniformity of sizes of the epidermis patterns;
   analyze inherent elements among the elements indicating the texture state of the skin based on the detected epidermis patterns; and
   evaluate the texture state of the skin based on the analysis result from the acquired elements and the analysis result from the inherent elements.

2. The image processing device according to claim 1, wherein the processing device analyzes, as the acquired elements, at least one of uniformity of shapes of the epidermis patterns or uniformity of distribution of edge directions of the epidermis patterns, and analyzes, as the inherent elements, the number of the epidermis patterns per unit area.

3. The image processing device according to claim 1, wherein the processing device calculates an evaluation value of the texture state of the skin by weighting and adding an evaluation value based on the analysis result from the acquired elements and an evaluation value based on the analysis result from the inherent elements.

4. The image processing device according to claim 1, wherein the epidermis patterns are patterns formed on the epidermis by skin ridges or skin grooves.

5. An image processing method performed by an image processing device configured to evaluate a texture state of skin, comprising:

detecting epidermis patterns that are patterns of an epidermis in an epidermis image captured from the epidermis of the skin;

analyzing acquired elements among elements indicating the texture state of the skin based on the detected epidermis patterns, wherein the acquired elements analyzed include uniformity of sizes of the epidermis patterns;

analyzing inherent elements among the elements indicating the texture state of the skin based on the detected epidermis patterns; and evaluating the texture state of the skin based on the analysis result from the acquired elements and the analysis result from the inherent elements.

6. A non-transitory storage medium configured to store a program for causing a computer to execute operations comprising:

detecting epidermis patterns that are patterns of an epidermis in an epidermis image captured from the epidermis of skin;

analyzing acquired elements among elements indicating a texture state of the skin based on the detected epidermis patterns;

analyzing inherent elements among the elements indicating the texture state of the skin based on the detected epidermis patterns, wherein the acquired elements analyzed include uniformity of sizes of the epidermis patterns; and evaluating the texture state of the skin based on the analysis result from the acquired elements and the analysis result from the inherent elements.

* * * * *